US011725037B2

(12) United States Patent
Hartmann et al.

(10) Patent No.: US 11,725,037 B2
(45) Date of Patent: *Aug. 15, 2023

(54) PEPTIDE DUAL AGONISTS OF GIPR AND GLP2R

(71) Applicant: University of Copenhagen, Copenhagen K (DK)

(72) Inventors: Bolette Hartmann, Hellerup (DK); Maria Buur Nordskov Gabe, Værløse (DK); Lærke Smidt Gasbjerg, Vanløse (DK); Mette Marie Rosenkilde, Hellerup (DK); Jens Juul Holst, Hellerup (DK)

(73) Assignee: University of Copenhagen, Copenhagen K (DK)

(*) Notice: Subject to any disclaimer, the term of this patent is extended or adjusted under 35 U.S.C. 154(b) by 12 days.

This patent is subject to a terminal disclaimer.

(21) Appl. No.: 17/007,407

(22) Filed: Aug. 31, 2020

(65) Prior Publication Data

US 2020/0392198 A1 Dec. 17, 2020

Related U.S. Application Data

(63) Continuation of application No. 16/341,082, filed as application No. PCT/EP2017/076060 on Oct. 12, 2017, now Pat. No. 10,774,127.

(51) Int. Cl.
| | | |
|---|---|---|
| *C07K 14/645* | (2006.01) | |
| *A61P 19/08* | (2006.01) | |
| *A61K 38/00* | (2006.01) | |
| *C07K 14/605* | (2006.01) | |

(52) U.S. Cl.
CPC ............ *C07K 14/645* (2013.01); *A61P 19/08* (2018.01); *C07K 14/605* (2013.01); *A61K 38/00* (2013.01)

(58) Field of Classification Search
CPC ........ C07K 14/645; A61P 19/08; A61K 38/00
See application file for complete search history.

(56) References Cited

U.S. PATENT DOCUMENTS

| | | | | |
|---|---|---|---|---|
| 2007/0212355 | A1* | 9/2007 | Baker | A61P 43/00 424/145.1 |
| 2009/0117104 | A1* | 5/2009 | Baker | A61P 1/00 424/133.1 |
| 2014/0221281 | A1* | 8/2014 | Haack | A61K 38/28 514/4.9 |
| 2015/0164996 | A1 | 6/2015 | Kadereit et al. | |

FOREIGN PATENT DOCUMENTS

| | | |
|---|---|---|
| WO | WO-1997/039031 | 10/1997 |
| WO | WO-2002/024214 A2 | 3/2002 |
| WO | WO-2004/103310 A2 | 12/2004 |
| WO | WO-2004/103390 A2 | 12/2004 |
| WO | WO-2005/003296 A2 | 1/2005 |
| WO | WO-2005/047297 A1 | 5/2005 |
| WO | WO-2006/017292 A1 | 2/2006 |
| WO | WO-2007/067828 A2 | 6/2007 |
| WO | WO-2008/028117 A2 | 3/2008 |
| WO | WO-2008/033395 A2 | 3/2008 |
| WO | WO-2008/113601 A1 | 9/2008 |
| WO | WO-2010/123930 A2 | 10/2010 |
| WO | WO-2012/034704 A1 | 3/2012 |
| WO | WO-2012/051431 A2 | 4/2012 |
| WO | WO-2012/138941 A1 | 10/2012 |
| WO | WO-2012/167744 A1 | 12/2012 |
| WO | WO-2013/003449 A2 | 1/2013 |
| WO | WO-2013/040093 A2 | 3/2013 |
| WO | WO-2013/070796 A2 | 5/2013 |
| WO | WO-2015/009991 A2 | 1/2015 |
| WO | WO-2015/038938 A1 | 3/2015 |
| WO | WO-2016/066818 A1 | 5/2016 |

OTHER PUBLICATIONS

Hanna, A. et al., The non-glycemic effects of incretin therapies on cardiovascular outcomes, cognitive function and bone health, Expert Rev. Endocrinol. Metab., 10(1): 101-114, 2015.

Hofbauer, L. et al., Osteoporosis in Patients With Diabetes Mellitus, Journal Of Bone And Mineral Research, 22(9): 1317-1328, May 14, 2007.

Just, R., The Novel GLP-1/GLP-2 Dual Agonist ZP-GG-72 Increases Intestinal Growth And Improves Insulin Sensitivity In Dio Mice, Jun. 16, 2014.

Meier, C. et al., Effects of Diabetes Drugs on the Skeleton, Bone, 82: 93-100, Apr. 23, 2015.

Nissen, A. et al., Glucose-Dependent Insulinotropic Polypeptide Inhibits Bone Resorption in Humans, J Clin Endocrinol Metab, 99(11):E2325-E2329, Nov. 2014.

WO2004/103310 A2 & DATABASE Geneseq [Online] Feb. 24, 2005 (Feb. 24, 2005), "Glucacon-like peptide 2 (E9D).", retrieved from EBI accession No. GSP :ADV25214.

WO1997/39031 A1 & DATABASE Geneseq [Online] May 7, 1998 (May 7, 1998), "Glucacon-like peptide-2 analogue [Thr5]hGLP-2(1-33).", retrieved from EBI accession No. GSP :AAW45331.

* cited by examiner

Primary Examiner — Amber D Steele
(74) Attorney, Agent, or Firm — Julie K. Staple; Dinsmore & Shohl LLP

(57) ABSTRACT

Provided herewith are peptide dual agonists of at least the GIPR (glucose-dependent insulinotropic polypeptide receptor) and the GLP2R (glucagon-like peptide-2 receptor), and their use for treatment of bone disorders such as osteoporosis.

19 Claims, 2 Drawing Sheets
Specification includes a Sequence Listing.

PEPTIDE DUAL AGONISTS OF GIPR AND GLP2R

REFERENCE TO RELATED APPLICATIONS

This application is a continuation of U.S. patent application Ser. No. 16/341,082, filed Apr. 11, 2019, now U.S. Pat. No. 10,774,127, which is a U.S. national stage application of PCT/EP2017/076060, filed Oct. 12, 2017, which claims priority to Denmark Application No. PA 2016 70799, filed Oct. 12, 2016. The entire content of each application is incorporated herein by reference.

FIELD OF THE INVENTION

The present invention relates to peptide dual agonists; or co-agonists; of the GIPR (glucose-dependent insulinotropic polypeptide receptor) and the GLP2R (glucagon-like peptide-2 receptor); and their use for treatment of bone disorders such as osteoporosis.

BACKGROUND OF THE INVENTION

Gastrointestinal peptides and adipokines are critical signalling molecules involved in controlling whole-body energy homeostasis. These circulating hormones regulate a variety of biological responses such as hunger, satiety and glucose uptake. In vivo experiments have established that these hormones also regulate bone metabolism, while associations between these hormones and bone mass have been observed in human clinical studies.

Incretins are gastrointestinal hormones that help to regulate carbohydrate metabolism in response to food intake. The two main incretins are glucose-dependent insulinotropic peptide (GIP) and glucagon-like peptide-1 (GLP-1), both secreted by intestinal epithelial cells. Intestinal glucagon-like peptide-2 (GLP-2) is co-secreted along with GLP-1 upon nutrient ingestion.

Gastrointestinal hormones released after meal ingestion, such as GIP and GLP-2 have been shown to regulate bone turnover; GIP has a positive effect on bone, and GLP-1 and GLP-2 regulate bone homeostasis and have a positive contribution to bone mass. However, their effects are often short-lived; therefore, other pharmacological interventions such as GLP-1R agonists and DPP-4 inhibitors in conjunction with GLP-2 injection are emerging as better candidates for preventing bone resorption.

Osteoporosis can be defined as a combination of reduced bone mass and altered bone quality, resulting in decreased bone strength with an increased risk of fractures. Gastrointestinal hormones including glucose-dependent insulinotropic peptide (GIP), glucagon-like peptide-1 (GLP-1) and glucagon-like peptide-1 (GLP-2) have each been implicated in bone metabolism and as potential therapies for treating osteoporosis.

GLP-2 and GLP-1 are suggested for treating osteoporosis, alone or in combination with anti-osteoporosis compounds (WO 2002/024214). A dual agonist of GIP and GLP-1 is disclosed in WO2012167744. A dual agonist of the glucagon receptor and for example GIP or GLP-2 is disclosed in WO2012138941. WO2015038938 refers to a GLP-1 R and GIPR dual agonist. Room for improvement remains in the potential therapy of bone disorders associated with reduced bone density, such as osteoporosis.

SUMMARY OF THE INVENTION

Dual agonists that combine the properties of GIP and GLP-2 receptor agonists are provided herewith. Peptide dual agonists designed from the native GIP and GLP-2 peptides that target at least GIPR and GLP-2R have not been disclosed previously.

It is an aspect to provide a peptide dual agonist comprising amino acids from hGIP (SEQ ID NO:22) and amino acids from hGLP-2 (SEQ ID NO:23), wherein said peptide is an agonist of GIPR (glucose-dependent insulinotropic polypeptide receptor) and of GLP2R (glucagon-like peptide-2 receptor).

In one embodiment said peptide comprises or consists of 20 to 42, such as 20 to 33 consecutive amino acids, such as 33 consecutive amino acids.

In one embodiment said peptide dual agonist is selected from the group consisting of any one of SEQ ID NO:s 1-21, 24 and 26 to 33, or a functional variant thereof, or a functional fragment thereof.

In one embodiment said peptide dual agonist is modified by attaching at least one fatty acid molecule at one or more amino acid residues of any one of SEQ ID NOs:1 to 21, 24 and 26 to 33, or a functional variant thereof, or a functional fragment thereof.

Also provided are fusion or conjugate peptides comprising the peptide dual agonist, nucleic acid constructs encoding the peptide dual agonist, and a multimeric compound comprising two or more peptide dual agonists.

Also provided is the peptide dual agonist for use as a medicament, such as for use in the treatment of a bone disorder.

DEFINITIONS

Figure 1:
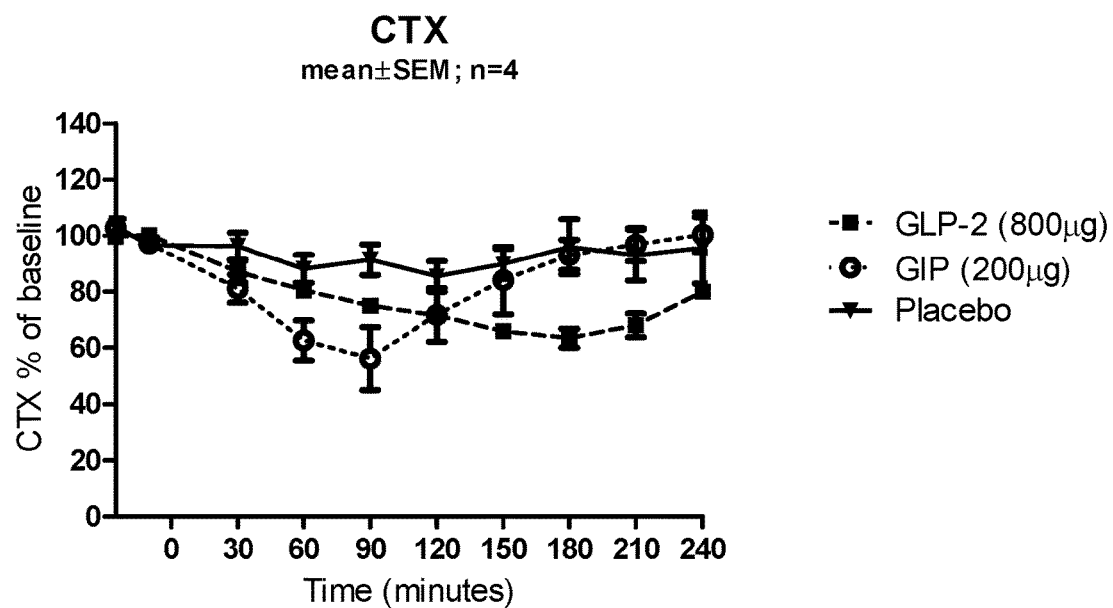
FIG. 1: Measurements of serum C-terminal cross-linking telopeptide of type I collagen (CTX) in blood samples collected at 30 minutes interval after injection of hGLP-2 alone, hGIP alone or placebo (cf. Example 3)

The term "affinity" refers to the strength of binding between a receptor and its ligand(s).

The term "agonist" in the present context refers to a peptide as defined herein, capable of binding to and activating a receptor.

The term "dual agonist" or "co-agonist" refers to a peptide as defined herein, capable of binding to and activating at least two receptors, wherein the at least two receptors are different receptors. In the present context a dual agonist is an agonist of GIPR and an agonist of the GLP2R. A dual agonist defined herewith may also have agonist activity towards additional receptors, whereby the dual agonist is an agonist of at least GIPR and GLP2R.

An "amino acid residue" can be a natural or non-natural amino acid residue linked by peptide bonds or bonds different from peptide bonds. The amino acid residues can be in D-configuration or L-configuration. An amino acid residue comprises an amino terminal part ($NH_2$) and a carboxy terminal part (COOH) separated by a central part comprising a carbon atom, or a chain of carbon atoms, at least one of which comprises at least one side chain or functional group. NH$_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b)(2) belong to the group of amino acids listed herewith: Y,G,F,M,A,S,I,L,T,V,P,K,H,Q,E,W,R,D,N and C. Non-natural amino acids are those not listed immediately above. Also, non-natural amino acid residues include, but are not limited to, modified amino acid residues, L-amino acid residues, and stereoisomers of D-amino acid residues.

An "equivalent amino acid residue" refers to an amino acid residue capable of replacing another amino acid residue in a polypeptide without substantially altering the structure and/or functionality of the polypeptide. Equivalent amino acids thus have similar properties such as bulkiness of the side-chain, side chain polarity (polar or non-polar), hydrophobicity (hydrophobic or hydrophilic), pH (acidic, neutral or basic) and side chain organization of carbon molecules (aromatic/aliphatic). As such, "equivalent amino acid residues" can be regarded as "conservative amino acid substitutions".

Within the meaning of the term "equivalent amino acid substitution" as applied herein, one amino acid may be substituted for another, in one embodiment, within the groups of amino acids indicated herein below:

Amino acids having polar side chains (Asp, Glu, Lys, Arg, His, Asn, Gln, Ser, Thr, Tyr, and Cys); Amino acids having non-polar side chains (Gly, Ala, Val, Leu, Ile, Phe, Trp, Pro, and Met); Amino acids having aliphatic side chains (Gly, Ala Val, Leu, Ile); Amino acids having cyclic side chains (Phe, Tyr, Trp, His, Pro); Amino acids having aromatic side chains (Phe, Tyr, Trp); Amino acids having acidic side chains (Asp, Glu); Amino acids having basic side chains (Lys, Arg, His); Amino acids having amide side chains (Asn, Gln); Amino acids having hydroxy side chains (Ser, Thr); Amino acids having sulphur-containing side chains (Cys, Met); Neutral, weakly hydrophobic amino acids (Pro, Ala, Gly, Ser, Thr); Hydrophilic, acidic amino acids (Gln, Asn, Glu, Asp); and Hydrophobic amino acids (Leu, Ile, Val).

Where the L or D form (optical isomers) has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

A "functional variant" of a peptide is a peptide capable of performing essentially the same functions as the peptide it is a functional variant of. In particular, a functional variant can bind the same molecules, preferably with the same affinity, as the peptide it is a functional variant of.

A "bioactive agent" (i.e. a biologically active substance/agent) is any agent, drug, compound, composition of matter or mixture which provides some pharmacologic, often beneficial, effect that can be demonstrated in vivo or in vitro. It refers to the peptide sequences defined herewith, compounds or compositions comprising these and nucleic acid constructs encoding said peptides. As used herein, this term further includes any physiologically or pharmacologically active substance that produces a localized or systemic effect in an individual. A 'bioactive agent' as used herein denotes collectively a peptide, a nucleic acid construct encoding said peptide, and a composition comprising a peptide.

The terms "drug" and "medicament" as used herein include biologically, physiologically, or pharmacologically active substances that act locally or systemically in the human or animal body.

The terms "treatment" and "treating" as used herein refer to the management and care of a patient for the purpose of combating a condition, disease or disorder. The term is intended to include the full spectrum of treatments for a given condition from which the patient is suffering, and refer equally to curative therapy, prophylactic or preventative therapy and ameliorating or palliative therapy, such as administration of the peptide or composition for the purpose of: alleviating or relieving symptoms or complications; delaying the progression of the condition, partially arresting the clinical manifestations, disease or disorder; curing or eliminating the condition, disease or disorder; amelioration or palliation of the condition or symptoms, and remission (whether partial or total), whether detectable or undetectable; and/or preventing or reducing the risk of acquiring the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The term "palliation", and variations thereof, as used herein, means that the extent and/or undesirable manifestations of a physiological condition or symptom are lessened and/or time course of the progression is slowed or lengthened, as compared to not administering compositions of the present invention.

The term "Individual" refers to vertebrates, particular members of the mammalian species, preferably primates including humans. As used herein, 'subject' and 'individual' may be used interchangeably. Treatment of animals, such as mice, rats, dogs, cats, cows, horses, sheep and pigs, is, however, also within the scope of the present invention.

An "individual in need thereof" refers to an individual who may benefit from treatment. In one embodiment, said individual in need thereof is a diseased individual, wherein said disease may be a bone disorder.

A "treatment effect" or "therapeutic effect" is manifested if there is a change in the condition being treated, as measured by the criteria constituting the definition of the terms "treating" and "treatment." There is a "change" in the condition being treated if there is at least 5% improvement, preferably 10% improvement, more preferably at least 25%, even more preferably at least 50%, such as at least 75%, and most preferably at least 100% improvement. The change can be based on improvements in the severity of the treated condition in an individual, or on a difference in the frequency of improved conditions in populations of individuals with and without treatment with the bioactive agent, or with the bioactive agent in combination with a pharmaceutical composition of the present invention.

A treatment according to the invention can be prophylactic, ameliorating and/or curative.

"Pharmacologically effective amount", "pharmaceutically effective amount" or "physiologically effective amount" of a "bioactive agent" is the amount of a bioactive agent present in a pharmaceutical composition as described herein that is needed to provide a desired level of active agent in the bloodstream or at the site of action in an individual (e.g. the lungs, the gastric system, the colorectal system, prostate, etc.) to be treated to give an anticipated physiological response when such composition is administered.

"Co-administering" or "co-administration" as used herein refers to the administration of one or more agonists and a state-of-the-art pharmaceutical composition. The at least two components can be administered separately, sequentially or simultaneously.

DETAILED DESCRIPTION OF THE INVENTION

GIP refers to glucose-dependent insulinotropic polypeptide, also known as Gastric Inhibitory Peptide (or polypeptide). As used herein the abbreviation hGIP is human GIP (Uniprot accession number P09681). GIP is derived from a 153-amino acid proprotein and circulates as a biologically active 42-amino acid peptide (positions 52-93). It is synthesized by K cells of the mucosa of the duodenum and the jejunum of the gastrointestinal tract.

Under physiological conditions the 42 amino acid hormone, GIP, is degraded by the enzyme dipeptidylpeptidase 4 (DPP-4), which cleaves at the third position of the GIP molecule to yield GIP3-42. GIP1-30 is produced as a result of post-translational processing. If GIP1-30 is secreted into the circulation in humans, the cleavage catalyzed by DPP-4 would result in GIP3-30.

The sequence of hGIP is:

```
                                        (SEQ ID NO: 22)
YAEGTFISDYSIAMDKIHQQDFVNWLLAQKGKKNDWKHNITQ.
```

GIPR (or GIP receptor) refers to gastric inhibitory polypeptide receptor(s). These seven-transmembrane proteins are found at least on beta-cells in the pancreas. As used herein the abbreviation hGIPR is human GIPR (Uniprot accession number P48546).

Several physiological effects of GIP have been identified. GIP induces insulin secretion stimulated primarily by hyperosmolarity of glucose in the duodenum. The amount of insulin secreted is greater when glucose is administered orally than intravenously. GIP is also thought to have significant effects on fatty acid metabolism through stimulation of lipoprotein lipase activity in adipocytes. GIP recently appeared as a major player in bone remodelling, and deficiency in GIP receptors has been associated with a dramatic decrease in bone quality and a subsequent increase in fracture risk.

Glucagon-like peptide-2 (GLP-2) is a 33 amino acid peptide in humans created by specific post-translational proteolytic cleavage of proglucagon in a process that also liberates the related glucagon-like peptide-1 (GLP-1) and glucagon itself. GLP-2 is produced by the intestinal endocrine L cell and by various neurons in the central nervous system. Intestinal GLP-2 is co-secreted along with GLP-1 upon nutrient ingestion. When externally administered, GLP-2 produces a number of effects in humans and rodents, including intestinal growth, enhancement of intestinal function, reduction in bone breakdown and neuroprotection. GLP-2 and related analogs have potential as treatments for short bowel syndrome, Crohn's disease, osteoporosis and as adjuvant therapy during cancer chemotherapy.

The sequence of hGLP-2 is:

```
                               (SEQ ID NO: 23)
HADGSFSDEMNTILDNLAARDFINWLIQTKITD
```

The GLP-2 receptor (GLP2R) is a G protein-coupled receptor superfamily member. GLP2R is expressed in the gut and closely related to the glucagon receptor (GCGR) and the receptor for GLP1 (GLP1R). As used herein the abbreviation hGLP2R is human GLP2R (e.g. Uniprot accession number O95838). As used herein the abbreviation hGLP1R is human GLP1R (GLP-1 receptor) (e.g. Uniprot accession number P43220).

Dual Agonist Peptides

The present inventors have designed novel GIP and GLP-2 peptide analogues, which peptides are agonists of GIPR and of GLP2R; i.e. are dual agonists of the GI PR and GLP2R. A dual agonist of the GI PR and GLP2R means that the peptide binds to and/or activates at least the GI PR and the GLP2R. This makes them potentially useful in a range of therapeutic applications.

The peptides are designed by combining amino acids/amino acid stretches from the GIP peptide (SEQ ID NO:22) and from the GLP-2 peptide (SEQ ID NO:23). These amino acids are preferably involved in one or more of receptor binding, receptor affinity, receptor activity and/or otherwise relevant for the agonist activity of the peptides.

It is an aspect to provide a peptide dual agonist comprising amino acids from hGIP (SEQ ID NO:22) and amino acids from hGLP-2 (SEQ ID NO:23), wherein said peptide is an agonist of GIPR (glucose-dependent insulinotropic polypeptide receptor) and is an agonist of GLP2R (glucagon-like peptide-2 receptor).

Said peptide dual agonist being an agonist of GIPR and an agonist of GLP2R imply that the peptide dual agonist is at least an agonist of GIPR and of GLP2R. It does not exclude that the peptide dual agonist can bind and/or activate further receptors.

In one embodiment the peptide dual agonist as defined herein is an agonist of GIPR and of GLP2R, as well as one or more further receptors. In one embodiment the peptide dual agonist as defined herein is an agonist of GIPR, of GLP2R, and of GLP1R (glucagon-like peptide-1 receptor).

Reference to GIPR, GLP2R, and GLP1R as used herein throughout can be substituted with hGIPR, hGLP2R, and hGLP1R.

In one embodiment the peptide dual agonist comprises amino acids from hGIP (SEQ ID NO: 22) which are involved in GIPR binding and/or GIPR activation; and amino acids from hGLP-2 (SEQ ID NO:23) which are involved in GLP2R binding and/or GLP2R activation.

In one embodiment the peptide dual agonist comprises
  a. amino acids from hGLP-2 (SEQ ID NO:23) and/or hGIP (SEQ ID NO:22) at the N-terminus,
  b. a central/N-terminal stretch of amino acids primarily from hGIP (SEQ ID NO:22),
  c. a central/C-terminal stretch of amino acids primarily from hGLP-2 (SEQ ID NO:23), and
  d. optionally amino acids primarily from hGIP (SEQ ID NO:22) at the C-terminus.

In one embodiment the peptide dual agonist comprises or consists of 20 to 42 consecutive amino acids; such as 20 to 22 amino acids, such as 22 to 24 amino acids, such as 24 to 26 amino acids, such as 26 to 28 amino acids, such as 28 to 30 amino acids, such as 30 to 32 amino acids, such as 32 to 34 amino acids, such as 34 to 36 amino acids, such as 36 to 38 amino acids, such as 38 to 40 amino acids, such as 40 to 42 consecutive amino acids as defined herein.

In one embodiment the peptide dual agonist comprises or consists of 20 to 42 consecutive amino acids; such as 20, 21, 22, 23, 24, 25, 26, 27, 28, 29, 30, 31, 32, 33, 34, 35, 36, 37, 38, 39, 40, 41 or 42 consecutive amino acids.

In one embodiment the peptide dual agonist comprises or consists of 20 to 33 consecutive amino acids, such as 20-21, such as 21-22, such as 22-23, such as 23-24, such as 24-25, such as 25-26, such as 26-27, such as 27-28, such as 28-29, such as 29-30, such as 30-31, such as 31-32, such as 32-33 consecutive amino acids.

In one embodiment the peptide dual agonist comprises or consists of 33 consecutive amino acids.

In one embodiment the peptide dual agonist comprises or consists of 20 to 42 consecutive amino acids, such as comprises or consist of 20 to 33 amino acids, wherein
  a. amino acids at positions 1 to 4 are from hGLP-2 (SEQ ID NO:23) and/or from hGIP (SEQ ID NO:22),
  b. amino acids at positions 5 to 11 are primarily from hGIP (SEQ ID NO:22),
  c. amino acids at positions 12 to 20, 12 to 30 or 12 to 33 are primarily from hGLP-2 (SEQ ID NO:23),
    such as amino acids at positions 12-20, 12-21, 12-22, 12-23, 12-24,12-25, 12-26, 12-27, 12-28, 12-29, 12-30, 12-31, 12-32, 12-33 primarily from hGLP-2 (SEQ ID NO:23), and
  d. optionally amino acids at positions 30-33 are primarily from hGIP (SEQ ID NO:22).

In one embodiment the peptide dual agonist comprises or consists of 20 to 42 consecutive amino acids, such as comprises or consist of 20 to 33 amino acids, wherein
  a. the amino acid at position 1 is from hGLP-2 (SEQ ID NO:23)
  b. amino acids at positions 2 to 4 are from hGLP-2 (SEQ ID NO:23) and/or from hGIP (SEQ ID NO:22),
  c. amino acids at positions 5 to 11 are primarily from hGIP (SEQ ID NO:22), and
  d. amino acids at positions 12 to 20 or 12 to 30 are primarily from hGLP-2 (SEQ ID NO:23),
    such as amino acids at positions 12-20, 12-21, 12-22, 12-23, 12-24,12-25, 12-26, 12-27, 12-28, 12-29, 12-30 primarily from hGLP-2 (SEQ ID NO:23), and
  e. amino acids at positions 30-33 are primarily from hGIP (SEQ ID NO:22) or primarily from hGLP-2 (SEQ ID NO:23).

In one embodiment amino acids at positions 12 to 20 or 12 to 30 are primarily from hGLP-2 (SEQ ID NO:23), and amino acids at positions 31-33 are primarily from hGIP (SEQ ID NO:22).

In one embodiment amino acids at positions 12 to 20 or 12 to 30 or 12 to 33 are primarily from hGLP-2 (SEQ ID NO:23).

In one embodiment when amino acids are defined as "primarily from" this means that at least 50% of the amino acids are from the peptide in question, such as at least 55%, such as at least 60%, such as at least 65%, such as at least 70%, such as at least 75%, such as at least 80%, such as at least 85%, such as at least 90%, such as at least 95%, such as 100% are from the peptide in question (i.e. from hGIP or from hGLP-2).

In one embodiment when amino acids are defined as "primarily from" this means that 50-55% of the amino acids are from the peptide in question, such as 55-60%, such as 60-65%, such as 65-70%, such as 70-75%, such as 75-80%, such as 80-85%, such as 85-90%, such as 90-95%, such as 95-100% are from the peptide in question (i.e. from hGIP or from hGLP-2).

When an amino acid is from hGIP or from hGLP-2, this means that the amino acid at a certain position of the peptide dual agonist corresponds to the amino acid at the same position of hGIP or hGLP-2. For instance, if the amino acid at position 1 is from GIP this means that the amino acid is "Y". If the amino acid at position 1 is from GLP-2 this means that the amino acid is "H".

It is also an aspect to provide a peptide dual agonist comprising or consisting of the sequence (SEQ ID NO: 20)
$HX_1X_2GX_3FX_4X_5X_6X_7X_8X_9X_{10}X_{11}DX_{12}LAARDFX_{13}$ $NWLX_{14}X_{15}X_{16}KX_{17}X_{18}X_{19}$, wherein $X_1$ to $X_{19}$ are individually any amino acid, such as a naturally occurring or a non-naturally occurring amino acid as defined herein, wherein said peptide is an agonist of GIPR and is an agonist of GLP2R.

In a particular embodiment $X_1$ is selected from A, G and V; $X_2$ is selected from D and E; $X_3$ is selected from T and S; $X_4$ is selected from I and S; $X_5$ is selected from S and D; $X_5$ is selected from D and E; $X_7$ is selected from Y and M; $X_5$ is selected from S and N; $X_9$ is selected from T and I; $X_{10}$ is selected from I and A; $X_{11}$ is selected from L and M; $X_{12}$ is selected from N and K; $X_{13}$ is selected from I and V; $X_{14}$ is selected from I and L; $X_{15}$ is selected from Q and A; $X_{16}$ is selected from T and Q; $X_{17}$ is selected from I and G; $X_{18}$ is selected from T and K; and/or $X_{19}$ is selected from D and K.

In one embodiment $X_{17}X_{18}X_{19}$ is selected from the group consisting of ITD, GKK, GTD, IKD and ITK. In one embodiment $X_{17}X_{18}X_{19}$ is ITD. In one embodiment $X_{17}X_{18}X_{19}$ is GKK.

It is a further aspect to provide a peptide dual agonist comprising or consisting of the sequence (SEQ ID NO: 20)
$HX_1X_2GX_3FX_4X_5X_6X_7X_8X_9X_{10}X_{11}DX_{12}$ $LAARDFX_{13}NWLX_{14}X_{15}X_{16}KX_{17}X_{18}X_{19}$, wherein $X_1$ is selected from A, G and V, $X_2$ is selected from D and E, $X_3$ is selected from T and S, $X_4$ is selected from I and S, $X_5$ is selected from S and D, $X_6$ is selected from D and E, $X_7$ is selected from Y and M, $X_8$ is selected from S and N, $X_9$ is selected from T and I, $X_{10}$ is selected from I and A, $X_{11}$ is selected from L and M, $X_{12}$ is selected from N and K, $X_{13}$ is selected from I and V, $X_{14}$ is selected from I and L, $X_{15}$ is selected from Q and A, $X_{16}$ is selected from T and Q, $X_{17}$ is selected from I and G, $X_{18}$ is selected from T and K, and $X_{19}$ is selected from D and K, or a functional variant thereof, or a functional fragment thereof.

SEQ ID NO:20 may also be written as H(A/G/V)(D/E)G(T/S)F(I/S)(S/D)(D/E)(Y/M)(S/N)(T/I)(I/A)(L/M)D(N/K)LAARDF(I/V)NWL(I/L) (Q/A)(T/Q)K(I/G)(T/K)(D/K); or a functional variant thereof, or a functional fragment thereof.

It is also an aspect to provide a peptide dual agonist comprising or consisting of the sequence $$HX_1X_2GX_3FX_4X_5X_6X_7X_8X_{30}X_{10}X_{31}DX_{12}LX_{32}$$
$$AX_{33}DFX_{13}NWLX_{14}X_{15}X_{16}KX_{17}X_{18}X_{19},$$
(SEQ ID NO: 33)

wherein $X_1$ to $X_{33}$ are individually any amino acid, such as a naturally occurring or a non-naturally occurring amino acid as defined herein,
wherein said peptide is an agonist of GIPR and is an agonist of GLP2R.

In a particular embodiment $X_1$ is selected from A, G and V; $X_2$ is selected from D and E; $X_3$ is selected from T and S; $X_4$ is selected from I and S; $X_5$ is selected from S and D; $X_8$ is selected from D and E; $X_7$ is selected from Y and M; $X_8$ is selected from S and N; $X_{30}$ is selected from T, I and K; $X_{10}$ is selected from I and A; $X_{31}$ is selected from L, M and K; $X_{12}$ is selected from N and K; $X_{32}$ is selected from A and K; $X_{33}$ is selected from A and K, $X_{13}$ is selected from I and V; $X_{14}$ is selected from I and L; $X_{15}$ is selected from Q and A; $X_{16}$ is selected from T and Q; $X_{17}$ is selected from I and G; $X_{18}$ is selected from T and K; and/or $X_{19}$ is selected from D and K.

In one embodiment $X_{17}X_{18}X_{19}$ is selected from the group consisting of ITD, GKK, GTD, IKD and ITK. In one embodiment $X_{17}X_{18}X_{19}$ is ITD. In one embodiment $X_{17}X_{18}X_{19}$ is GKK.

It is a further aspect to provide a peptide dual agonist comprising or consisting of the sequence $$HX_1X_2GX_3FX_4X_5X_6X_7X_8X_{30}X_{10}X_{31}DX_{12}LX_{32}AX_{33}$$
$$DFX_{13}NWLX_{14}X_{15}X_{16}KX_{17}X_{18}X_{19},$$
(SEQ ID NO: 33)

wherein $X_1$ is selected from A, G and V,
$X_2$ is selected from D and E,
$X_3$ is selected from T and S,
$X_4$ is selected from I and S,
$X_5$ is selected from S and D,
$X_5$ is selected from D and E,
$X_7$ is selected from Y and M,
$X_5$ is selected from S and N,
$X_{35}$ is selected from T, I and K,
$X_{10}$ is selected from I and A,
$X_{31}$ is selected from L, M and K,
$X_{12}$ is selected from N and K,
$X_{32}$ is selected from A and K,
$X_{33}$ is selected from A and K,
$X_{13}$ is selected from I and V,
$X_{14}$ is selected from I and L,
$X_{15}$ is selected from Q and A,
$X_{16}$ is selected from T and Q,
$X_{17}$ is selected from I and G,
$X_{18}$ is selected from T and K, and
$X_{19}$ is selected from D and K, or a functional variant thereof, or a functional fragment thereof.

SEQ ID NO:33 may also be written as H(A/G/V)(D/E)G(T/S)F(I/S)(S/D)(D/E)(Y/M)(S/N)(T/I/K)(I/A)(L/M/K)D(N/K)L(A/K)A(R/K)DF(I/V)NWL(I/L)(Q/A)(T/Q)K(I/G)(T/K)(D/K); or a functional variant thereof, or a functional fragment thereof.

It is also an aspect to provide a peptide dual agonist comprising or consisting of the sequence $$HX_{20}X_{21}GTFISDYSTILDNLAARDFX_{22}NWLX_{23}X_{24}X_{25}KX_{26}X_{27}X_{28}$$
(SEQ ID NO: 21)

wherein $X_{20}$ to $X_{28}$ are individually amino acid, such as a naturally occurring or a non-naturally occurring amino acid as defined herein, wherein said peptide is an agonist of GIPR and is an agonist of GLP2R.

In a particular embodiment $X_{20}$ is selected from A and G; $X_{21}$ is selected from D and E; $X_{22}$ is selected from I and V; $X_{23}$ is selected from I and L; $X_{24}$ is selected from Q and A; $X_{25}$ is selected from T and Q; $X_{28}$ is selected from I and G; $X_{27}$ is selected from T and K; and/or $X_{28}$ is selected from D and K.

In one embodiment $X_{26}X_{27}X_{28}$ is selected from the group consisting of ITD, GKK, GTD, IKD and ITK. In one embodiment $X_{26}X_{27}X_{28}$ is ITD. In one embodiment $X_{26}X_{27}X_{28}$ is GKK.

It is a further aspect to provide a peptide dual agonist comprising or consisting of the sequence $$HX_{20}X_{21}GTFISDYSTILDNLAARDFX_{22}NWLX_{23}X_{24}X_{25}KX_{26}X_{27}X_{28}$$
(SEQ ID NO: 21)

wherein $X_{20}$ is selected from A and G,
$X_{21}$ is selected from D and E,
$X_{22}$ is selected from I and V,
$X_{23}$ is selected from I and L,
$X_{24}$ is selected from Q and A,
$X_{25}$ is selected from T and Q,
$X_{28}$ is selected from I and G,
$X_{27}$ is selected from T and K, and
$X_{28}$ is selected from D and K,
or a functional variant thereof, or a functional fragment thereof.

SEQ ID NO:21 may also be written as H(A/G)(D/E)GTFISDYSTILDNLAARDF(IN)NWL(I/L)(Q/A)(T/Q)K(I/G)(T/K)(D/K); or a functional variant thereof, or a functional fragment thereof.

In one embodiment the peptide dual agonist is selected from the group consisting of (Co-1)
(SEQ ID NO: 1)
HAEGTFISDYSTILDNLAARDFINWLIQTKITD, (Co-2)
(SEQ ID NO: 2)
HAEGTFISDYSTILDNLAARDFINWLIQTKITDNDWKHNITQ, (Co-3)
(SEQ ID NO: 3)
HADGTFISDYSTILDNLAARDFINWLIQTKITD, (Co-4)
(SEQ ID NO: 4)
HAEGSFISDYSTILDNLAARDFINWLIQTKITD, (Co-5)
(SEQ ID NO: 5)
HAEGTFSDEYSTILDNLAARDFINWLIQTKITD, (Co-6)
(SEQ ID NO: 6)
HAEGTFISDMNTILDNLAARDFINWLIQTKITD, (Co-7)

```
                                           (SEQ ID NO: 7)
HAEGTFISDYSIAMDKLAARDFINWLIQTKITD, (Co-8)
                                           (SEQ ID NO: 8)
HAEGTFISDYSTILDNIHQQDFINWLIQTKITD, (Co-9)
                                           (SEQ ID NO: 9)
HAEGTFISDYSTILDNLAARDFVNWLLAQKITD, (Co-10)
                                           (SEQ ID NO: 10)
HAEGTFISDYSTILDNLAARDFINWLIQTKGKK, (Co-11)
                                           (SEQ ID NO: 11)
HGDGTFISDYSTILDNLAARDFINWLIQTKITD, (Co-12)
                                           (SEQ ID NO: 12)
HVDGTFISDYSTILDNLAARDFINWLIQTKITD, (Co-13)
                                           (SEQ ID NO: 13)
HADGTFSSDYSTILDNLAARDFINWLIQTKITD, (Co-14)
                                           (SEQ ID NO: 14)
HADGTFIDDYSTILDNLAARDFINWLIQTKITD, (Co-15)
                                           (SEQ ID NO: 15)
HADGTFISEYSTILDNLAARDFINWLIQTKITD, (Co-16)
                                           (SEQ ID NO: 16)
HADGTFISDYSTILDNLAARDFINWLIQTKGTD, (Co-17)
                                           (SEQ ID NO: 17)
HADGTFISDYSTILDNLAARDFINWLIQTKIKD, (Co-18)
                                           (SEQ ID NO: 18)
HADGTFISDYSTILDNLAARDFINWLIQTKITK, (Co-19)
                                           (SEQ ID NO: 19)
HADGTFISDYSTILDNLAARDFINWLIQTKGKK, (Co-20)
                                           (SEQ ID NO: 26)
HADGTFSSDYSTILDNLAAKDFINWLIQTKITD, (Co-24)
                                           (SEQ ID NO: 27)
HADGTFISDYSKILDNLAARDFINWLIQTKITK, (Co-25)
                                           (SEQ ID NO: 28)
HADGTFISDYSTIKDNLAARDFINWLIQTKITK, (Co-26)
                                           (SEQ ID NO: 29)
HADGTFISDYSTILDKLAARDFINWLIQTKITK, (Co-27)
                                           (SEQ ID NO: 30)
HADGTFISDYSTILDNLKARDFINWLIQTKITK, (Co-28),
                                           (SEQ ID NO: 31)
HADGTFISDYSTILDNLAAKDFINWLIQTKITK
and (Co-34)
                                           (SEQ ID NO: 32)
HADGTFISDYSTILDNLAARDFINWLIQTKGKKNDWKHNITQ,
``` or a functional variant thereof, or a functional fragment thereof.

In one embodiment the peptide dual agonist comprises or consists of the sequence HADGTFISDYSTILDNLAARDFINWLIQTKITD (SEQ ID NO:3), or a functional variant or a functional fragment thereof.

In one embodiment the peptide dual agonist comprises or consists of the sequence HAEGTFISDYSTILDNLAARDFINWLIQTKGKK (SEQ ID NO:10) (Co-10), or a functional variant or a functional fragment thereof.

In one embodiment the peptide dual agonist comprises or consists of the sequence HADGTFISDYSTILDNLAARDFINWLIQTKITK (SEQ ID NO:18), or a functional variant or a functional fragment thereof.

In one embodiment the peptide dual agonist comprises or consists of the sequence HADGTFISDYSTILDNLAARDFINWLIQTKGKK (SEQ ID NO:19), or a functional variant or a functional fragment thereof.

In one embodiment the peptide dual agonist comprises or consists of the sequence $HX_{29}DGTFISDYSTILDNLAARDFINWLIQTKITD$ (SEQ ID NO:24), wherein $X_{29}$ is any amino acid, such as a naturally occurring or a non-naturally occurring amino acid as defined herein, or a functional variant or a functional fragment thereof.

In one embodiment the peptide dual agonist comprises or consists of the sequence $HX_{29}DGTFISDYSTILDNLAARDFINWLIQTKITD$ (SEQ ID NO:24), wherein $X_{29}$ is selected from A, G and V, or a functional variant or a functional fragment thereof.

In one embodiment the amino acid at position 2 of the peptide dual agonists defined herein as SEQ ID NOs:1 to 21, 24 and 26 to 33, in one embodiment corresponding to $X_1$, $X_{20}$ or $X_{29}$, is any amino acid, such as a naturally occurring or a non-naturally occurring amino acid as defined herein. In one embodiment the amino acid at position 2 of the peptide dual agonists, in one embodiment corresponding to $X_1$, $X_{20}$ or $X_{29}$, is selected from the group consisting of A, G and V. In one embodiment the amino acid at position 2 of the peptide dual agonists, in one embodiment corresponding to $X_1$, $X_{20}$ or $X_{29}$, is a non-naturally occurring amino acid.

A peptide that comprises or consists of a sequence means that the peptide can comprise the sequence, consist of the sequence, or comprise at least the full sequence. A peptide that comprises a peptide sequence, such as comprising the sequence HADGTFISDYSTILDNLAARDFINWLIQTKITD (SEQ ID NO:3), means that the peptide includes all of the peptide sequence HADGTFISDYSTILDNLAARDFINWLIQTKITD (SEQ ID NO:3). It does, however, not exclude that additional components or amino acids are present.

In one embodiment the dual agonist peptides defined herein comprises additional amino acids at the C-terminus, such as comprises the amino acids corresponding to all or some of the amino acids at position 34 to 42 of hGIP (hGIP is SEQ ID NO:22); namely NDWKHNITQ (SEQ ID NO:25) or a variant or fragment thereof.

In one embodiment a functional variant of a peptide dual agonist has at least 60% sequence identity, such as at least 70% sequence identity, such as at least 75% sequence identity, such as at least 80% sequence identity, such as at least 85% sequence identity, such as at least 90% sequence identity, such as at least 95% sequence identity, such as at least 97% sequence identity to said peptide dual agonist.

In one embodiment a functional variant of a peptide dual agonist has 60 to 65% sequence identity, such as 65 to 70% sequence identity, such as 70 to 75% sequence identity, such as 75 to 80% sequence identity, such as 80 to 85% sequence identity, such as 85 to 90% sequence identity, such as 90 to 95% sequence identity, such as 95 to 99% sequence identity, such as 99 to 100% sequence identity to said peptide dual agonist. 'Identity' and 'sequence identity' may be used interchangeably herein.

In one embodiment a functional variant comprises one or more amino acid substitutions, such as 1 to 8 amino acid substitutions, such as 1 to 2, 2 to 3, 3 to 4, 4 to 5, 5 to 6, 6 to 7 or 7 to 8 amino acid substitutions.

In one embodiment a functional variant comprises one amino acid substitution, two amino acid substitutions, three amino acid substitutions, four amino acid substitutions or five amino acid substitutions.

In one embodiment said amino acid substitutions are conservative amino acid substitutions. In one embodiment said functional variant comprises one or more conservative amino acid substitutions.

A conservative substitution (or synonymous substitution) is the substitution of amino acids whose side chains have similar biochemical properties and thus do not affect the function of the peptide.

Among the common amino acids, for example, a "conservative amino acid substitution" can also be illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

In one embodiment, a serine residue of a peptide disclosed herein is substituted with an amino acid selected from the group consisting of Gln, Asn and Thr (all amino acids with polar uncharged side chains); and independently thereof, a glycine residue (Gly) is substituted with an amino acid selected from the group consisting of Ala, Val, Leu, and Ile; and independently thereof, an arginine residue (Arg) is substituted with an amino acid selected from the group consisting of Lys and His (all have positively charged side chains); and independently thereof, a lysine residue (Lys) is substituted with an amino acid selected from the group consisting of Arg and His; and independently thereof, a methionine residue (Met) is substituted with an amino acid selected from the group consisting of Leu, Pro, Ile, Val, Phe, Tyr and Trp (all have hydrophobic side chains); and independently thereof, a glutamine residue (Gln) is substituted with an amino acid selected from the group consisting of Asp, Glu, and Asn; and independently thereof, an alanine residue (Ala) is substituted with an amino acid selected from the group consisting of Gly, Val, Leu, and Ile.

Particular amino acid substitutions as defined herein are K to R, E to D, L to M, Q to E, I to V, I to L, A to S, Y to W, K to Q, S to T, N to S and Q to R.

Other particular amino acid substitutions as defined herein are T to K, L to K, N to K, A to K and R to K.

The identity between amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90, or by simple comparison of the specific amino acids present at corresponding positions in two peptide sequences to be compared. Homology may be used as a synonym to identity/sequence identity.

Conservative substitutions may be introduced in any one or more positions of a peptide according to the present disclosure, as long as the variant remains functional. It may however also be desirable to introduce non-conservative substitutions in one or more positions (non-synonymous substitutions).

A non-conservative substitution leading to the formation of a variant of the peptide in one embodiment comprises substitution of amino acid residues that i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids can in one embodiment be made based upon their hydrophobicity and hydrophilicity values and the relative similarity of the amino acid side-chain substituents, including charge, size, and the like.

The peptides according to the present invention comprise proteinogenic or natural amino acids, i.e. the 22 amino acids naturally incorporated into polypeptides. Of these, 20 are encoded by the universal genetic code and the remaining 2; selenocysteine (Sec, U) and pyrrolysine (Pyl, O), are incorporated into proteins by unique synthetic mechanisms.

A peptide according to the present disclosure in one embodiment comprises one or more non-naturally occurring amino acid residues (unnatural, non-proteinogenic or non-standard amino acids). Non-naturally occurring amino acids include e.g., without limitation, beta-2-naphthyl-alanine, trans-3-methylproline, 2,4-methanoproline, cis-4-hydroxyproline, ornithine, trans-4-hydroxyproline, N-methylglycine, allo-threonine, methylthreonine, hydroxyethylcysteine, hydroxyethyl homocysteine, nitroglutamnine, homoglutamine, pipecolic acid, thiazolidine carboxylic acid, dehydroproline, 3- and 4-methylproline, 3,3-dimethylproline, tert-leucine, norleucine, norvaline, 2-azaphenylalanine, 3-azaphenylalanine, 4-azaphenylalanine, and 4-fluorophenylalanine.

Any amino acids as defined herein may be in the L- or D-configuration. If nothing is specified, reference to the L-isomeric form is preferably meant.

The standard and/or non-standard amino acids may be linked by peptide bonds (to form a linear peptide chain), or by non-peptide bonds (e.g. via the variable side-chains of the amino acids). Preferably, the amino acids of the present disclosure are linked by peptide bonds.

In one embodiment said peptide dual agonist is truncated at the C-terminus.

In one embodiment said functional fragment comprises or consists of amino acids 1 to 33 of any one of SEQ ID NOs:1 to 21, 24 and 26 to 33.

In one embodiment said functional fragment comprises or consists of amino acids 1 to 32 of any one of SEQ ID NOs: to 21, 24 and 26 to 33, such as amino acids 1 to 31, such as amino acids 1 to 30, such as amino acids 1 to 29, such as amino acids 1 to 28, such as amino acids 1 to 27, such as amino acids 1 to 26, such as amino acids 1 to 25, such as amino acids 1 to 24, such as amino acids 1 to 23, such as amino acids 1 to 22, such as amino acids 1 to 21, such as amino acids 1 to 20, such as amino acids 1 to 19, such as amino acids 1 to 18, such as amino acids 1 to 17, such as amino acids 1 to 16, such as amino acids 1 to 15 of any one of SEQ ID NOs: to 21, 24 and 26 to 33.

The terms 'peptide' and 'isolated peptide' may be used interchangeably herein. The terms 'variant' and 'functional variant' may be used interchangeably herein. The terms 'fragment' and 'functional fragment' may be used interchangeably herein. When reference is made to a 'peptide' herewith, this term will encompass both references to a peptide per se, and also to a peptide for use as defined herein.

In one embodiment the peptide is non-naturally occurring.

In one embodiment the peptide is synthetic.

In one embodiment the peptide is an isolated peptide.

In one embodiment the peptide is a labeled peptide, such as radiolabeled or fluorescent labeled peptide.

In another embodiment, a variant as defined herein includes sequences wherein an alkyl amino acid is substituted for an alkyl amino acid, wherein an aromatic amino acid is substituted for an aromatic amino acid, wherein a sulfur-containing amino acid is substituted for a sulfur-containing amino acid, wherein a hydroxy-containing amino acid is substituted for a hydroxy-containing amino acid, wherein an acidic amino acid is substituted for an acidic amino acid, wherein a basic amino acid is substituted for a basic amino acid, and/or wherein a dibasic monocarboxylic amino acid is substituted for a dibasic monocarboxylic amino acid.

The term peptide also embraces post-translational modifications introduced by chemical or enzyme-catalyzed reactions, as are known in the art. These include acetylation, phosphorylation, methylation, glucosylation, glycation, amidation, hydroxylation, deimination, deamidation, carbamylation and sulfation of one or more amino acid residues, and also proteolytic modification by known proteinases including lysosomal kathepsins, and also calpains, secretases and matrix-metalloproteinases.

In one embodiment the peptide dual agonist defined herein is C-terminally amidated (—NH$_2$).

In one embodiment the peptide dual agonist defined herein is N-terminally acetylated (COCH$_3$).

Also, functional equivalents of the peptides may comprise chemical modifications such as ubiquitination, labeling (e.g., with radionuclides, various enzymes, etc.), pegylation (derivatization with polyethylene glycol), or by insertion (or substitution by chemical synthesis) of amino acids such as ornithine, which do not normally occur in human proteins (non-proteinogenic).

Sterically similar compounds may be formulated to mimic the key portions of the peptide structure. This may be achieved by techniques of modelling and chemical designing known to those of skill in the art. For example, esterification and other alkylations may be employed to modify the amino terminus of e.g. a di-arginine peptide backbone, to mimic a tetra peptide structure. It will be understood that all such sterically similar constructs fall within the scope of the present invention. Peptides with N-terminal and C-terminal alkylations and esterifications are also encompassed within the present invention.

A contiguous or consecutive peptide sequence is a sequence of consecutive amino acids being linked linearly by peptide bonds. Contiguous and consecutive amino acid sequence is used interchangeably herein.

A functional variant and functional fragment as used herein means that the variant or fragment of the peptide dual agonist retain all or some of the functions associated with the said peptide dual agonist, i.e. they retain at least some effect associated with the native sequence.

In one embodiment a functional variant or fragment retains the same biological activity or capabilities as the native peptide or the peptide from which it is derived.

In one embodiment the peptide dual agonist including functional variants or fragments thereof is capable of one or more of:
a. binding to GIPR and GLP2R, and/or
b. activation of GIPR and GLP2R, and/or
c. stimulation of GIPR- and GLP2R activation, such as GIPR- and GLP2R-mediated cAMP production, and/or
d. inhibiting bone resorption, and/or
e. stimulating bone formation.

In one embodiment the peptide dual agonist as well as functional variants or fragments thereof is a full agonist of GIPR and GLP2R.

In one embodiment the peptide dual agonists are capable of binding to and activating GIPR. In some embodiments, the GIPR is the human GIPR (Uniprot accession number P48546). In one embodiment the peptide dual agonists are capable of binding to and activating GLP2R. In some embodiments, the GLP2R is the human GLP2R (Uniprot accession number O95838).

In one embodiment the peptide dual agonists provided herewith are capable of
activating the GIPR with an efficacy ($E_{max}$ values) which is at least 65% of the efficacy by which native GIP activates the GIPR, such as at least 70%, such as at least 75%, such as at least 80%, such as at least 85%, such as at least 90%, such as at least 95% of the efficacy by which native GIP activates the GIPR; and
activating the GLP2R with an efficacy ($E_{max}$ values) which is at least 65% of the efficacy by which native GLP-2 activates the GLP2R, such as at least 70%, such as at least 75%, such as at least 80%, such as at least 85%, such as at least 90%, such as at least 95% of the efficacy by which native GLP-2 activates the GLP2R.

In one embodiment the peptide dual agonists provided herewith are capable of
activating the GIPR with an efficacy ($E_{max}$ values) which is at least 65-70% of the efficacy by which native GIP activates the GIPR, such as at least 70-75%, such as at least 75-80%, such as at least 80-85%, such as at least 85-90%, such as at least 90-95%, such as at least 95-100% of the efficacy by which native GIP activates the GIPR; and
activating the GLP2R with an efficacy ($E_{max}$ values) which is at least 65-70% of the efficacy by which native GLP-2 activates the GLP2R, such as at least 70-75%, such as at least 75-80%, such as at least 80-85%, such as at least 85-90%, such as at least 90-95%, such as at least 95-100% of the efficacy by which native GLP-2 activates the GLP2R.

In one embodiment the peptide dual agonists provided herewith are capable of
activating the GI PR with the same or increased potency by which native GIP activates the GIPR; and
activating the GLP2R with the same or increased potency by which native GLP-2 activates the GLP2R.

In one embodiment the peptide dual agonists are capable of binding to and activating one or more further receptors, besides GI PR and GLP2R. In one embodiment the peptide dual agonists are capable of binding to and activating GLP1R. In some embodiments, the GLP1R is the human GI PR (Uniprot accession number P43220).

Also provided herewith is a fusion or conjugate peptide comprising the peptide dual agonist disclosed herein.

In one embodiment the conjugate peptide comprises one or more half-life extending moieties attached to said dual agonist, such as covalently attached, in order to extend the serum half-life of the dual agonist peptide. In one embodiment a natural albumin ligand such as one or more fatty acids has been conjugated to the dual agonist peptides.

Acylated Dual Agonist Peptides

In some embodiments of the present disclosure the peptide dual agonists disclosed herein are acylated, which in some embodiments increase half-life and in vivo stability while retaining the surprising agonistic properties.

One embodiment of the present disclosure provides a peptide dual agonist, wherein said peptide is modified by attaching at least one fatty acid molecule at one or more amino acid residues of any one of SEQ ID NOs:1 to 21, 24 and 26 to 33 or a functional variant thereof, or a functional fragment thereof.

One embodiment of the present disclosure provides a peptide dual agonist, wherein said peptide is modified by attaching at least one fatty acid molecule at the N-terminal amino acid residue of any one of SEQ ID NOs:1 to 21, 24 and 26 to 33 or a functional variant thereof, or a functional fragment thereof.

One embodiment of the present disclosure provides a peptide dual agonist, wherein said peptide is modified by attaching at least one fatty acid molecule at the C-terminal amino acid residue of any one of SEQ ID NOs:1 to 21, 24 and 26 to 33 or a functional variant thereof, or a functional fragment thereof.

One embodiment of the present disclosure provides a peptide dual agonist, wherein said peptide is modified by attaching at least one fatty acid molecule at one or more lysine residues, such as at one or more amino acid residues modified to a lysine, of any one of SEQ ID NOs:1 to 21, 24 and 26 to 33 or a functional variant thereof, or a functional fragment thereof.

One embodiment of the present disclosure provides a peptide dual agonist comprising or consisting of the sequence (SEQ ID NO: 20)
$HX_1X_2GX_3FX_4X_5X_6X_7X_8X_9X_{10}X_{11}DX_{12}L$
$AARDFX_{13}NWLX_{14}X_{15}X_{16}KX_{17}X_{18}X_{19}$, wherein $X_1$ to $X_{19}$ are individually any amino acid, such as a naturally occurring or a non-naturally occurring amino acid as defined herein, wherein said peptide is an agonist of GIPR and is an agonist of GLP2R, and wherein said peptide dual agonist is modified by attaching at least one fatty acid molecule at one or more amino acid residues of said sequence.

One embodiment of the present disclosure provides a peptide dual agonist comprising or consisting of the sequence (SEQ ID NO: 21)
$HX_{20}X_{21}GTFISDYSTILDNLAARD$
$FX_{22}NWLX_{23}X_{24}X_{25}KX_{26}X_{27}X_{28}$, wherein $X_{20}$ to $X_{28}$ are individually any amino acid, such as a naturally occurring or a non-naturally occurring amino acid as defined herein, wherein said peptide is an agonist of GIPR and is an agonist of GLP2R, and wherein said peptide dual agonist is modified by attaching at least one fatty acid molecule at one or more amino acid residues of said sequence.

One embodiment of the present disclosure provides a peptide dual agonist comprising or consisting of the sequence (SEQ ID NO: 33)
$HX_1X_2GX_3FX_4X_5X_6X_7X_8X_{30}X_{10}X_{31}DX_{12}LX_{32}$ $AX_{33}DFX_{13}NWLX_{14}X_{15}X_{16}KX_{17}X_{18}X_{19}$, wherein $X_1$ to $X_{33}$ are individually any amino acid, such as a naturally occurring or a non-naturally occurring amino acid as defined herein, wherein said peptide is an agonist of GIPR and is an agonist of GLP2R, and wherein said peptide dual agonist is modified by attaching at least one fatty acid molecule at one or more amino acid residues of said sequence.

In one embodiment the peptide dual agonist is selected from the group consisting of

```
(Co-1)
                                    (SEQ ID NO: 1)
HAEGTFISDYSTILDNLAARDFINWLIQTKITD, (Co-2)
                                    (SEQ ID NO: 2)
HAEGTFISDYSTILDNLAARDFINWLIQTKITDNDWKHNITQ, (Co-3)
                                    (SEQ ID NO: 3)
HADGTFISDYSTILDNLAARDFINWLIQTKITD, (Co-4)
                                    (SEQ ID NO: 4)
HAEGSFISDYSTILDNLAARDFINWLIQTKITD, (Co-5)
                                    (SEQ ID NO: 5)
HAEGTFSDEYSTILDNLAARDFINWLIQTKITD, (Co-6)
                                    (SEQ ID NO: 6)
HAEGTFISDMNTILDNLAARDFINWLIQTKITD, (Co-7)
                                    (SEQ ID NO: 7)
HAEGTFISDYSIAMDKLAARDFINWLIQTKITD, (Co-8)
                                    (SEQ ID NO: 8)
HAEGTFISDYSTILDNIHQQDFINWLIQTKITD, (Co-9)
                                    (SEQ ID NO: 9)
HAEGTFISDYSTILDNLAARDFVNWLLAQKITD, (Co-10)
                                    (SEQ ID NO: 10)
HAEGTFISDYSTILDNLAARDFINWLIQTKGKK, (Co-11)
                                    (SEQ ID NO: 11)
HGDGTFISDYSTILDNLAARDFINWLIQTKITD, (Co-12)
                                    (SEQ ID NO: 12)
HVDGTFISDYSTILDNLAARDFINWLIQTKITD, (Co-13)
                                    (SEQ ID NO: 13)
HADGTFSSDYSTILDNLAARDFINWLIQTKITD, (Co-14)
                                    (SEQ ID NO: 14)
HADGTFIDDYSTILDNLAARDFINWLIQTKITD,
```

-continued (Co-15)
HADGTFISEYSTILDNLAARDFINWLIQTKITD, (SEQ ID NO: 15)

(Co-16)
HADGTFISDYSTILDNLAARDFINWLIQTKGTD, (SEQ ID NO: 16)

(Co-17)
HADGTFISDYSTILDNLAARDFINWLIQTKIKD, (SEQ ID NO: 17)

(Co-18)
HADGTFISDYSTILDNLAARDFINWLIQTKITK, (SEQ ID NO: 18)

(Co-19)
HADGTFISDYSTILDNLAARDFINWLIQTKGKK, (SEQ ID NO: 19)

(Co-20)
HADGTFSSDYSTILDNLAAKDFINWLIQTKITD, (SEQ ID NO: 26)

(Co-24)
HADGTFISDYSKILDNLAARDFINWLIQTKITK, (SEQ ID NO: 27)

(Co-25)
HADGTFISDYSTIKDNLAARDFINWLIQTKITK, (SEQ ID NO: 28)

(Co-26)
HADGTFISDYSTILDKLAARDFINWLIQTKITK, (SEQ ID NO: 29)

(Co-27)
HADGTFISDYSTILDNLKARDFINWLIQTKITK, (SEQ ID NO: 30)

(Co-28)
HADGTFISDYSTILDNLAAKDFINWLIQTKITK, (SEQ ID NO: 31)
and (Co-34)
HADGTFISDYSTILDNLAARDFINWLIQTKGKKNDWKHNITQ (SEQ ID NO: 32)

or a functional variant thereof, or a functional fragment thereof, and wherein said peptide dual agonist is modified by attaching at least one fatty acid molecule at one or more amino acid residues of said sequence.

In one embodiment the fatty acid is a straight-chain fatty acid.

In one embodiment the fatty acid is a branched fatty acid.

In one embodiment the fatty acid molecule is a monoacyl fatty acid molecule, comprising one fatty acid.

In one embodiment the fatty acid molecule is a diacyl fatty acid molecule.

In one embodiment the fatty acid molecule according to the present disclosure is a diacyl fatty acid molecule comprising two fatty acids.

In one embodiment the fatty acid molecule according to the present disclosure is a diacyl fatty acid molecule containing two carboxyl functional groups.

In one embodiment the fatty acid molecule comprises an acyl group of the formula $CH_3(CH_2)_nCO—$, wherein n in an integer from 4 to 24.

In one embodiment the fatty acid molecule comprises an acyl group of the formula $CH_3(CH_2)_nCO—$, wherein n in an integer from 4 to 24, such as 6 to 20, such as 8 to 18, such as 10-16.

In one embodiment the fatty acid molecule comprises one or more acyl groups selected from the group consisting of $CH_3(CH_2)_6CO—$, $CH_3(CH_2)_8CO—$, $CH_3(CH_2)_{10}CO—$, $CH_3(CH_2)_{12}CO—$, $CH_3(CH_2)_{14}O—$, $CH_3(CH_2)_{16}CO—$, $CH_3(CH_2)_{18}CO—$, $CH_3(CH_2)_{20}CO—$ and $CH_3(CH_2)_{22}CO—$.

In one embodiment the fatty acid molecule comprises an acyl group selected from the group consisting of $CH_3(CH_2)_{10}CO—$ (lauryl, C12), $CH_3(CH_2)_{12}CO—$ (myristoyl, C14), $CH_3(CH_2)_{14}O—$ (palmitoyl, C16) and $CH_3(CH_2)_{16}CO—$ (stearyl, C18).

In one embodiment the fatty acid molecule comprises an acyl group of the formula $COOH(CH_2)_nCO—$ (dicarboxylic acid), wherein n in an integer from 4 to 24, such as 6 to 20, such as 8 to 18, such as 10-16.

In one embodiment the fatty acid molecule comprises an acyl group selected from the group consisting of $COOH(CH_2)_{14}CO—$, $COOH(CH_2)_{16}CO—$, $COOH(CH_2)_{18}CO—$ and $COOH(CH_2)_{20}CO—$.

In one embodiment said fatty acid molecule is selected from C12, C14, C16 and C18.

In one embodiment said fatty acid molecule is selected from C14 diacid, C16 diacid and C18 diacid.

In one embodiment said fatty acid molecule is C12 (lauryl).

In one embodiment said fatty acid molecule is C14 (myristoyl).

In one embodiment said fatty acid molecule is C16 (palmitoyl).

In one embodiment said fatty acid molecule is 1,16-Hexadecanedioic acid/hexadecanedioic acid.

It follows that C12 is the fatty acid $CH_3(CH_2)_{10}CO—$ (lauryl); C14 is the fatty acid $CH_3(CH_2)_{12}CO—$ (myristoyl); C16 is the fatty acid $CH_3(CH_2)_{14}O—$ (palmitoyl) and C18 is the fatty acid $CH_3(CH_2)_{16}CO—$ (stearyl). The suffix "-diacid" means that the fatty acid molecule is a diacyl fatty acid molecule. No such suffix refers to a monoacyl fatty acid molecule.

A fatty acid molecule may be attached to an amino acid residue in such a way that a carboxyl group of the fatty acid molecule forms an amide bond with an amino group of the amino acid residue.

Attachment of fatty acid molecules to a peptide herein can occur either directly or indirectly, i.e. via a linker or spacer.

In one embodiment the fatty acid molecule is attached to an amino acid residue directly.

In one embodiment the fatty acid molecule is attached to an amino acid residue via a spacer.

In one embodiment the fatty acid molecule according to the present disclosure is directly attached to the alpha-amino group of an amino acid residue, wherein said amino acid residue is the N-terminal amino acid residue.

In one embodiment the fatty acid molecule according to the present disclosure is directly attached to the alpha-amino group of an amino acid residue, wherein said amino acid residue is the C-terminal amino acid residue.

In one embodiment a fatty acid molecule is attached to one or more amino acid residues having a side-chain aminoalkyl group ($—C_nH_{2n}NH_2$).

In one embodiment a fatty acid molecule is attached to one or more amino acid residues having a side-chain amino group ($NH_2$). In one embodiment an amino acid residue having a side-chain amino group ($NH_2$) is selected from the group consisting of Lys and Orn (ornithine).

In one embodiment the fatty acid molecule according to the present disclosure is directly attached to the epsilon-amino group of a Lys residue (Lys, K). Said Lysine residue can be a native Lys residue, or it can be introduced by way of mutation.

In one embodiment the amino acid residue having a fatty acid molecule attached is Lys.

In one embodiment the fatty acid molecule according to the present disclosure is directly attached to the epsilon-amino group of a Orn residue (Ornithine). Said Orn residue can be introduced by way of mutation.

In one embodiment the fatty acid molecule according to the present disclosure is attached to the alpha-amino group of the N-terminal amino acid residue of a peptide selected from the group consisting of:

```
(Co-1)
                                    (SEQ ID NO: 1)
HAEGTFISDYSTILDNLAARDFINWLIQTKITD, (Co-2)
                                    (SEQ ID NO: 2)
HAEGTFISDYSTILDNLAARDFINWLIQTKITDNDWKHNITQ, (Co-3)
                                    (SEQ ID NO: 3)
HADGTFISDYSTILDNLAARDFINWLIQTKITD, (Co-4)
                                    (SEQ ID NO: 4)
HAEGSFISDYSTILDNLAARDFINWLIQTKITD, (Co-5)
                                    (SEQ ID NO: 5)
HAEGTFSDEYSTILDNLAARDFINWLIQTKITD, (Co-6)
                                    (SEQ ID NO: 6)
HAEGTFISDMNTILDNLAARDFINWLIQTKITD, (Co-7)
                                    (SEQ ID NO: 7)
HAEGTFISDYSIAMDKLAARDFINWLIQTKITD, (Co-8)
                                    (SEQ ID NO: 8)
HAEGTFISDYSTILDNIHQQDFINWLIQTKITD, (Co-9)
                                    (SEQ ID NO: 9)
HAEGTFISDYSTILDNLAARDFVNWLLAQKITD, (Co-10)
                                    (SEQ ID NO: 10)
HAEGTFISDYSTILDNLAARDFINWLIQTKGKK, (Co-11)
                                    (SEQ ID NO: 11)
HGDGTFISDYSTILDNLAARDFINWLIQTKITD, (Co-12)
                                    (SEQ ID NO: 12)
HVDGTFISDYSTILDNLAARDFINWLIQTKITD, (Co-13)
                                    (SEQ ID NO: 13)
HADGTFSSDYSTILDNLAARDFINWLIQTKITD, (Co-14)
                                    (SEQ ID NO: 14)
HADGTFIDDYSTILDNLAARDFINWLIQTKITD, (Co-15)
                                    (SEQ ID NO: 15)
HADGTFISEYSTILDNLAARDFINWLIQTKITD, (Co-16)
                                    (SEQ ID NO: 16)
HADGTFISDYSTILDNLAARDFINWLIQTKGTD, (Co-17)
                                    (SEQ ID NO: 17)
HADGTFISDYSTILDNLAARDFINWLIQTKIKD, (Co-18)
                                    (SEQ ID NO: 18)
HADGTFISDYSTILDNLAARDFINWLIQTKITK, (Co-19)
                                    (SEQ ID NO: 19)
HADGTFISDYSTILDNLAARDFINWLIQTKGKK, (Co-20)
                                    (SEQ ID NO: 26)
HADGTFSSDYSTILDNLAAKDFINWLIQTKITD, (Co-24)
                                    (SEQ ID NO: 27)
HADGTFISDYSKILDNLAARDFINWLIQTKITK, (Co-25)
                                    (SEQ ID NO: 28)
HADGTFISDYSTIKDNLAARDFINWLIQTKITK, (Co-26)
                                    (SEQ ID NO: 29)
HADGTFISDYSTILDKLAARDFINWLIQTKITK, (Co-27)
                                    (SEQ ID NO: 30)
HADGTFISDYSTILDNLKARDFINWLIQTKITK, (Co-28)
                                    (SEQ ID NO: 31)
HADGTFISDYSTILDNLAAKDFINWLIQTKITK,
and (Co-34)
                                    (SEQ ID NO: 32)
HADGTFISDYSTILDNLAARDFINWLIQTKGKKNDWKHNITQ
``` or a functional variant thereof, or a functional fragment thereof.

In one embodiment the fatty acid molecule according to the present disclosure is attached to the alpha-amino group of the C-terminal amino acid residue of a peptide selected from the group consisting of:

```
(Co-1)
                                    (SEQ ID NO: 1)
HAEGTFISDYSTILDNLAARDFINWLIQTKITD, (Co-2)
                                    (SEQ ID NO: 2)
HAEGTFISDYSTILDNLAARDFINWLIQTKITDNDWKHNITQ, (Co-3)
                                    (SEQ ID NO: 3)
HADGTFISDYSTILDNLAARDFINWLIQTKITD, (Co-4)
                                    (SEQ ID NO: 4)
HAEGSFISDYSTILDNLAARDFINWLIQTKITD, (Co-5)
                                    (SEQ ID NO: 5)
HAEGTFSDEYSTILDNLAARDFINWLIQTKITD, (Co-6)
                                    (SEQ ID NO: 6)
HAEGTFISDMNTILDNLAARDFINWLIQTKITD, (Co-7)
                                    (SEQ ID NO: 7)
HAEGTFISDYSIAMDKLAARDFINWLIQTKITD, (Co-8)
                                    (SEQ ID NO: 8)
HAEGTFISDYSTILDNIHQQDFINWLIQTKITD,
```

(Co-1)
(SEQ ID NO: 1)
HAEGTFISDYSTILDNLAARDFINWLIQTKITD, (Co-2)
(SEQ ID NO: 2)
HAEGTFISDYSTILDNLAARDFINWLIQTKITDNDWKHNITQ, (Co-3)
(SEQ ID NO: 3)
HADGTFISDYSTILDNLAARDFINWLIQTKITD, (Co-4)
(SEQ ID NO: 4)
HAEGSFISDYSTILDNLAARDFINWLIQTKITD, (Co-5)
(SEQ ID NO: 5)
HAEGTFSDEYSTILDNLAARDFINWLIQTKITD, (Co-6)
(SEQ ID NO: 6)
HAEGTFISDMNTILDNLAARDFINWLIQTKITD, (Co-7)
(SEQ ID NO: 7)
HAEGTFISDYSIAMDKLAARDFINWLIQTKITD, (Co-8)
(SEQ ID NO: 8)
HAEGTFISDYSTILDNIHQQDFINWLIQTKITD, (Co-9)
(SEQ ID NO: 9)
HAEGTFISDYSTILDNLAARDFVNWLLAQKITD, (Co-10)
(SEQ ID NO: 10)
HAEGTFISDYSTILDNLAARDFINWLIQTKGKK, (Co-11)
(SEQ ID NO: 11)
HGDGTFISDYSTILDNLAARDFINWLIQTKITD, (Co-12)
(SEQ ID NO: 12)
HVDGTFISDYSTILDNLAARDFINWLIQTKITD, (Co-13)
(SEQ ID NO: 13)
HADGTFSSDYSTILDNLAARDFINWLIQTKITD, (Co-14)
(SEQ ID NO: 14)
HADGTFIDDYSTILDNLAARDFINWLIQTKITD, (Co-15)
(SEQ ID NO: 15)
HADGTFISEYSTILDNLAARDFINWLIQTKITD, (Co-16)
(SEQ ID NO: 16)
HADGTFISDYSTILDNLAARDFINWLIQTKGTD, (Co-17)
(SEQ ID NO: 17)
HADGTFISDYSTILDNLAARDFINWLIQTKIKD, (Co-18)
(SEQ ID NO: 18)
HADGTFISDYSTILDNLAARDFINWLIQTKITK, (Co-19)
(SEQ ID NO: 19)
HADGTFISDYSTILDNLAARDFINWLIQTKGKK, (Co-20)
(SEQ ID NO: 26)
HADGTFSSDYSTILDNLAAKDFINWLIQTKITD, (Co-24)
(SEQ ID NO: 27)
HADGTFISDYSKILDNLAARDFINWLIQTKITK, (Co-25)
(SEQ ID NO: 28)
HADGTFISDYSTIKDNLAARDFINWLIQTKITK, (Co-26)
(SEQ ID NO: 29)
HADGTFISDYSTILDKLAARDFINWLIQTKITK, (Co-27)
(SEQ ID NO: 30)
HADGTFISDYSTILDNLKARDFINWLIQTKITK, (Co-28)
(SEQ ID NO: 31)
HADGTFISDYSTILDNLAAKDFINWLIQTKITK,
and (Co-34)
(SEQ ID NO: 32)
HADGTFISDYSTILDNLAARDFINWLIQTKGKKNDWKHNITQ or a functional variant thereof, or a functional fragment thereof.

In one embodiment the fatty acid molecule according to the present disclosure is attached to the epsilon-amino group of any amino acid residue, such as a lysine residue, of a peptide selected from the group consisting of:

-continued (Co-24)
(SEQ ID NO: 27)
HADGTFISDYSKILDNLAARDFINWLIQTKITK, (Co-25)
(SEQ ID NO: 28)
HADGTFISDYSTIKDNLAARDFINWLIQTKITK, (Co-26)
(SEQ ID NO: 29)
HADGTFISDYSTILDKLAARDFINWLIQTKITK, (Co-27)
(SEQ ID NO: 30)
HADGTFISDYSTILDNLKARDFINWLIQTKITK, (Co-28)
(SEQ ID NO: 31)
HADGTFISDYSTILDNLAAKDFINWLIQTKITK,
and (Co-34)
(SEQ ID NO: 32)
HADGTFISDYSTILDNLAARDFINWLIQTKGKKNDWKHNITQ or a functional variant thereof, or a functional fragment thereof.

In one embodiment the fatty acid molecule according to the present disclosure is attached to the alpha-amino group of an amino acid residue via a linker or spacer, wherein said amino acid residue is the N-terminal amino acid residue.

In one embodiment the fatty acid molecule according to the present disclosure is attached to the alpha-amino group of an amino acid residue via a linker or spacer, wherein said amino acid residue is the C-terminal amino acid residue.

In one embodiment the fatty acid molecule according to the present disclosure is attached to the epsilon-amino group of a Lys residue via linker or spacer.

In one embodiment the fatty acid molecule according to the present disclosure is attached to the delta-amino group of an Orn residue via linker or spacer.

In one embodiment the fatty acid molecule may be attached to an amino acid residue by means of a spacer (or linker) in such a way that a carboxyl group of the spacer forms an amide bond with an amino group of the fatty acid molecule.

In one embodiment the spacer is an α,ω-amino acid. Examples of suitable spacers are succinic acid, Lys, Glu or Asp, or a dipeptide such as Gly-Lys. When the spacer is succinic acid, one carboxyl group thereof may form an amide bond with an amino group of the amino acid residue, and the other carboxyl group thereof may form an amide bond with an amino group of the fatty acid molecule. When the spacer is Lys, Glu or Asp, the carboxyl group thereof may form an amide bond with an amino group of the amino acid residue, and the amino group thereof may form an amide bond with a carboxyl group of the fatty acid molecule. When Lys is used as the spacer, a further spacer may in some instances be inserted between the ε-amino group of Lys and the fatty acid molecule. In one embodiment such a further spacer is succinic acid which forms an amide bond with the ε-amino group of Lys and with an amino group present in the fatty acid molecule. Other spacers are Nε-(γ-L-glutamyl), Nε-(β-L-asparagyl), Nε-glycyl, and Nε-(α-(γ-aminobutanoyl)).

In one embodiment the spacer is a hydrophilic linker. In one embodiment the spacer is a non-natural amino acid hydrophilic linker.

In one embodiment the spacer is selected from the group consisting of γ-aminobutanoyl (γ-aminobutyric acid), γ-glutamyl (γ-glutamic acid), β-asparagyl, β-alanyl and glycyl. In one embodiment the spacer comprises one or more of γ-aminobutanoyl (γ-aminobutyric acid), γ-glutamyl (γ-glutamic acid), β-asparagyl, β-alanyl and glycyl.

In one embodiment the spacer is a repeat of individual spacer moieties. In one embodiment the spacer is a repeat of identical spacer moieties. In one embodiment the spacer is a repeat of different spacer moieties.

In one embodiment the spacer is γ-glutamic acid-β-amino-3,6-dioxaoctanoic acid (γ-Glu)-AEEAc), or a repeat thereof.

In one embodiment the spacer is an amino acid residue except Cys. In one embodiment the spacer is 4-Abu. In one embodiment the spacer is γ-aminobuturic acid.

In another embodiment the spacer is a dipeptide, such as a dipeptide wherein the C-terminal amino acid residue is Lys, His or Trp, preferably Lys, and wherein the N-terminal amino acid residue is selected from the group comprising Ala, Arg, Asp, Asn, Gly, Glu, Gln, Ile, Leu, Val, Phe and Pro. In one embodiment the dipeptide spacer is Gly-Lys.

In one embodiment the spacer comprises one or more moieties selected from the group consisting of γ-aminobutanoyl (γ-aminobutyric acid), γ-glutamyl (γ-glutamic acid), β-asparagyl, β-alanyl and glycyl. In one embodiment the spacer comprises one or more of γ-aminobutanoyl (γ-aminobutyric acid), γ-glutamyl (γ-glutamic acid), β-asparagyl, β-alanyl, glycyl, γ-glutamic acid-β-amino-3,6-dioxaoctanoic acid (γ-Glu-AEEAc), an amino acid residue except Cys, 4-Abu, γ-aminobuturic acid and a dipeptide.

In another embodiment spacer is an unbranched alkane α,ω-dicarboxylic acid group having from 1 to 7 methylene groups, preferably two methylene groups, which spacer forms a bridge between an amino group of the parent peptide and an amino group of the fatty acid molecule.

In one embodiment the peptide dual agonist comprises or consists of the sequence (SEQ ID NO: 18)
H(C16/1)ADGTFISDYSTILDNLAARDFINWLIQTKITK.

In one embodiment the peptide dual agonist comprises or consists of the SEQ ID NO:18 and is acylated on position 1, i.e. the amino acid residue in position one, a His residue, is modified with the fatty acid chain C16.

In one embodiment the peptide dual agonist comprises or consists of the sequence (SEQ ID NO: 18)
HADGTFISDYSTILDNLAARDFINWLIQTK(C12/30)ITK.

In one embodiment the peptide dual agonist comprises or consists of the SEQ ID NO:18 and is acylated on position 30, i.e. the amino acid residue in position thirty, a Lys residue, is modified with the fatty acid chain C12.

In one embodiment the peptide dual agonist comprises or consists of the sequence (SEQ ID NO: 18)
HADGTFISDYSTILDNLAARDFINWLIQTK(C16/30)ITK.

In one embodiment the peptide dual agonist comprises or consists of the SEQ ID NO:18 and is acylated on position 30, i.e. the amino acid residue in position thirty, a Lys residue, is modified with the fatty acid chain C16.

In one embodiment the peptide dual agonist comprises or consists of the sequence (SEQ ID NO: 18)
HADGTFISDYSTILDNLAARDFINWLIQTKITK(C12/33).

In one embodiment the peptide dual agonist comprises or consists of the SEQ ID NO:18 and is acylated on position 33, i.e. the amino acid residue in position thirty-three, a Lys residue, is modified with the fatty acid chain C12.

In one embodiment the peptide dual agonist comprises or consists of the sequence (SEQ ID NO: 18)
HADGTFISDYSTILDNLAARDFINWLIQTKITK(C16/33).

In one embodiment the peptide dual agonist comprises or consists of the SEQ ID NO:18 and is acylated on position 33, i.e. the amino acid residue in position thirty-three, a Lys residue, is modified with the fatty acid chain C16.

In one embodiment the peptide dual agonist comprises or consists of the sequence (SEQ ID NO: 19)
HADGTFISDYSTILDNLAARDFINWLIQTKGK(C12/32)K.

In one embodiment the peptide dual agonist comprises or consists of the SEQ ID NO:19 and is acylated on position 32, i.e. the amino acid residue in position thirty-two, a Lys residue, is modified with the fatty acid chain C12.

In one embodiment the peptide dual agonist comprises or consists of the sequence (SEQ ID NO: 19)
HADGTFISDYSTILDNLAARDFINWLIQTKGK(C16/32)K.

In one embodiment the peptide dual agonist comprises or consists of the SEQ ID NO:19 and is acylated on position 32, i.e. the amino acid residue in position thirty-two, a Lys residue, is modified with the fatty acid chain C16.

In one embodiment the peptide dual agonist comprises or consists of the sequence (SEQ ID NO: 20)
HADGTFSSDYSTILDNLAAK(C16/20)DFINWLIQTKITD.

In one embodiment the peptide dual agonist comprises or consists of the SEQ ID NO:20 and is acylated on position 20, i.e. the amino acid residue in position twenty, a Lys residue, is modified with the fatty acid chain C16.

In one embodiment the peptide dual agonist comprises or consists of the sequence (SEQ ID NO: 20)
H(C16/1)ADGTFSSDYSTILDNLAARDFINWLIQTKITD.

In one embodiment the peptide dual agonist comprises or consists of the SEQ ID NO:20 and is acylated on position 1, i.e. the amino acid residue in position one, a His residue, is modified with the fatty acid chain C16.

In one embodiment the peptide dual agonist comprises or consists of the sequence (SEQ ID NO: 20)
HADGTFSSDYSTILDNLAARDFINWLIQTK(C16/30)ITD.

In one embodiment the peptide dual agonist comprises or consists of the SEQ ID NO:20 and is acylated on position 30, i.e. the amino acid residue in position thirty, a Lys residue, is modified with the fatty acid chain C16.

Compound

It is an aspect to provide a compound comprising or consisting of a dual agonist peptide as defined herein. In one embodiment, said peptide is formulated as a monomer (i.e. comprising 1 copy of the peptide), whereas in another embodiment, said peptide is formulated as a multimer.

Multimeric Compound

In one embodiment the peptide according to the present disclosure is formulated as a multimer. A multimer is a protein comprising or consisting of multiple monomers. A multimer is an aggregate of multiple molecules that is usually held together with non-covalent bonds. This definition distinguishes a multimer from a polymer, which is a series of monomers that are held together with covalent bonds.

A peptide sequence of the present disclosure is in one embodiment connected to another (identical or non-identical) peptide sequence of the present invention by a chemical bond or through a linker group. In some embodiments a peptide is formulated as an oligomer or multimer of monomers, wherein each monomer is as a peptide sequence as defined herein.

Thus, according to the disclosure a multimeric compound is in one embodiment a polymer comprising two or more peptide sequences of the invention, said peptide sequences being identical or non-identical, wherein at least one of the two or more peptide sequences is a peptide according to the present invention. Preferably, both peptide sequences are a peptide according to the present invention.

In one embodiment the multimeric compound is a dimer, comprising two peptides according to the present disclosure, said two peptides being identical or non-identical with respect to each other.

In another embodiment the multimeric compound is a trimer, comprising three peptides according to the present disclosure, said peptides being identical or non-identical with respect to each other.

In another embodiment the multimeric compound is a tetramer, comprising four peptides according to the present disclosure, said peptides being identical or non-identical with respect to each other.

In one embodiment the multimeric compound is a dendrimer, such as a tetrameric or octameric dendrimer. Dendrimers are repeatedly branched, roughly spherical large molecules, typically symmetric around the core, and often adopts a spherical three-dimensional morphology.

Dendrimers according to the present disclosure may comprise 4 peptides, 8 peptides, 16 peptides, or 32 peptides. In one particular embodiment said dendrimer comprises four peptides (i.e. a tetrameric dendrimer) or eight peptides (octameric dendrimer).

In some particular embodiments, the multimeric compound comprises two identical amino acid sequences of the present invention (dimer) or the compound comprises four identical copies of an amino acid sequence of the present invention (tetrameric dendrimer).

Provided herewith is a multimeric compound comprising
a. two or more peptides, wherein each of said two or more peptides are a dual agonist peptide according to any of the preceding claims, and
b. optionally a linker group.

In one embodiment the multimeric compound is selected from the group consisting of a dimer, a trimer, a tetramer, a tetrameric dendrimer and an octameric dendrimer.

The multimers according to the invention is in one embodiment made by linking two or more peptide monomers via a peptide bond or a linker group. In one embodiment they are linked to a lysine backbone, such as a lysine residue (each peptide chain is linked to a single lysine residue), or coupled to a polymer carrier, for example a protein carrier. Said linker group in one embodiment comprises a plurality of lysine residues, such as a core moiety having a plurality of lysine residues, such as seen in a lysine-based dendromeric structure containing three, seven, fifteen and more lysine residues However, any other linking of peptide monomers known to the skilled person may be envisioned.

The linking in one embodiment occurs at the N-terminal and/or C-terminal end of the peptide monomers.

Medicament/Medical Use

It is an aspect of the present disclosure to provide a peptide dual agonist, a nucleic acid construct encoding a peptide dual agonist, a delivery vehicle comprising a nucleic acid construct encoding a peptide dual agonist, as well a composition comprising the peptide dual agonist, as defined herein elsewhere, for use as a medicament.

A peptide dual agonist as defined herein is in one embodiment selected from the group consisting of SEQ ID NO:s 1 to 33, or a functional variant thereof, or a functional fragment thereof. In a further embodiment said peptide dual agonist as defined herein is modified by attaching at least one fatty acid molecule at one or more amino acid residues.

It is thus an aspect of the present disclosure to provide a peptide dual agonist as defined herein for use in a method of inhibiting bone resorption and/or stimulating bone formation.

Also disclosed is a peptide dual agonist selected from the group consisting of SEQ ID NO:s 1 to 33, or a functional variant thereof, or a functional fragment thereof, for use in a method of inhibiting bone resorption and/or stimulating bone formation.

Also provided is the use of a peptide dual agonist as defined herein for the manufacture of a medicament for inhibiting bone resorption and/or stimulating bone formation.

Also provided is a method of inhibiting bone resorption and/or stimulating bone formation, said method comprising administering a therapeutically effective amount of a peptide dual agonist as defined herein to an individual in need thereof.

It is a further aspect of the present disclosure to provide a peptide dual agonist as defined herein for use in a method of treating a bone disorder. In one embodiment the bone disorder is a disorder associated with increased bone resorption and/or reduced bone formation. In one embodiment the bone disorder is associated with poor or reduced bone density.

Also provided is a peptide dual agonist as defined herein for use in a method of treating a bone disorder, including treating, preventing and alleviating said bone disorder.

Also disclosed is a peptide dual agonist selected from the group consisting of SEQ ID NO:s 1 to 33, or a functional variant thereof, or a functional fragment thereof, for use in a method of treating a bone disorder.

Bone density or bone mineral density (BMD) is the amount of bone mineral in bone tissue.

The concept is of mass of mineral per volume of bone (relating to density in the physics sense), although clinically it is measured by proxy according to optical density per square centimeter of bone surface upon imaging. Bone density measurement is used in clinical medicine as an indirect indicator of osteoporosis/osteopenia and fracture risk. It is measured by a procedure called densitometry. There is a statistical association between poor bone density and higher probability of fracture. Bone density measurements are used to screen people for osteoporosis risk and to identify those who might benefit from measures to improve bone strength.

The T-score is the relevant measure when screening for osteoporosis. It is the bone mineral density (BMD) at the site when compared to the young normal reference mean. The criteria of the World Health Organization are:
Normal is a T-score of −1.0 or higher
Osteopenia is defined as between −1.0 and −2.5
Osteoporosis is defined as −2.5 or lower, meaning a bone density that is two and a half standard deviations below the mean of a young normal reference.

In one embodiment the bone disorder is associated with a T-score of −1.0 or lower, such as between −1.0 and −2.5, such as −2.5 or lower.

In one embodiment there is provided the use of a peptide dual agonist as defined herein for the manufacture of a medicament for treating a bone disorder.

Also provided is a method of treating a bone disorder, said method comprising administering a therapeutically effective amount of a peptide dual agonist as defined herein to an individual in need thereof.

An individual in need as referred to herein, is an individual that may benefit from the administration of a dual agonist peptide. Such an individual may suffer from a bone disorder or be in risk of suffering therefrom. The individual may be any human being, male or female, infant, middle-aged or old. The disorder to be treated or prevented in the individual may relate to the age of the individual, the general health of the individual, the medications used for treating the individual and whether or not the individual has a prior history of suffering from diseases or disorders that may have or have induced a bone density disorder.

In one embodiment the bone disorder is selected from the group consisting of osteopenia, osteoporosis, severe osteoporosis, osteomalacia, rickets, osteitis fibrosa cystica (OFC) and Paget's disease of bone.

In one embodiment the bone disorder is osteopenia.
In one embodiment the bone disorder is osteoporosis.

Also disclosed is a peptide dual agonist selected from the group consisting of SEQ ID NO:s 1 to 33, or a functional variant thereof, or a functional fragment thereof, for use in a method of treating a bone disorder selected from the group consisting of osteopenia, osteoporosis, severe osteoporosis, osteomalacia, rickets, osteitis fibrosa cystica (OFC) and Paget's disease of bone.

In one embodiment there is provided a peptide dual agonist selected from the group consisting of SEQ ID NO:s 1 to 33, or a functional variant thereof, or a functional fragment thereof, for use in a method of treating osteopenia.

In one embodiment there is provided a peptide dual agonist selected from the group consisting of SEQ ID NO:s 1 to 33, or a functional variant thereof, or a functional fragment thereof, for use in a method of treating osteoporosis.

Combination Therapy

It is also an aspect to provide a peptide dual agonist as defined herein for use in combination with a further active pharmaceutical ingredient. Said further active ingredient is in one embodiment useful for treating a bone disorder, such as a bone disorder associated with reduced bone density.

In one embodiment the further active pharmaceutical ingredient is selected from the group consisting of Bisphosphonates including Alendronate (Fosamax), Risedronate (Actonel, Atelvia, Benet), Ibandronate (Boniva), Zoledronic acid (Reclast, Aclasta, Zometa), Etidronic acid (Didronel), Pamidronic acid (Aredia/Pamimed), Tiludronic acid (Skelid); estrogen replacement therapy; hormone therapies; hormone-like medications including raloxifene (Evista); Calcitonin (Fortical and Miacalcin), Denosumab (Prolia); Teriparatide (Forteo); Vitamin D (alfacalcidol or calcitriol); calcium or phosphorus supplement.

In one embodiment the further active pharmaceutical ingredient increases the half-life of the present peptide dual agonist. In one embodiment the further active pharmaceutical ingredient is an inhibitor of dipeptidyl peptidase 4 (DPP-4/DDP-IV inhibitors), or gliptins. Examples include Sitagliptin, Vildagliptin, Saxagliptin, Linagliptin, Gemigliptin, Anagliptin, Teneligliptin, Alogliptin, Trelagliptin, Dutogliptin, and Omarigliptin (MK-3102).

Nucleic Acid Construct Encoding Dual Agonist Peptide

In one embodiment there is provided a nucleic acid construct encoding a dual agonist peptide as defined herein. In one embodiment said nucleic acid construct will be able to continuously express said peptide for a prolonged period of time; such as at least 1 month, for example at least 2 months, such as at least 3 months, for example at least 4 months, such as at least 5 months, for example at least 6 months, such as at least 7 months, for example at least 8 months, such as at least 9 months, for example at least 12 months.

It is thus an aspect to provide a nucleic acid construct encoding a peptide dual agonist as defined herewith.

In one embodiment there is provided a nucleic acid construct encoding a peptide dual agonist comprising amino acids from hGIP (SEQ ID NO:22) and amino acids from hGLP-2 (SEQ ID NO:23), wherein said peptide is an agonist of GIPR (glucose-dependent insulinotropic polypeptide receptor) and is an agonist of GLP2R (glucagon-like peptide-2 receptor); as defined herein.

In one embodiment there is provided a nucleic acid construct encoding a peptide dual agonist selected from the group consisting of SEQ ID NO:s 1 to 33, or a functional variant thereof, or a functional fragment thereof.

It is also an aspect to provide a nucleic acid construct encoding a dual agonist peptide as defined herein for use in a method of treating a bone disorder.

By nucleic acid construct is understood a genetically engineered nucleic acid. The nucleic acid construct may be a non-replicating and linear nucleic acid, a circular expression vector or an autonomously replicating plasmid. A nucleic acid construct may comprise several elements such as, but not limited to genes or fragments of same, promoters, enhancers, terminators, poly-A tails, linkers, polylinkers, operative linkers, multiple cloning sites (MCS), markers, STOP codons, internal ribosomal entry sites (IRES) and host homologous sequences for integration or other defined elements. It is to be understood that the nucleic acid construct according to the present invention may comprise all or a subset of any combination of the above-mentioned elements.

Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989). Further, nucleic acid constructs according to the present invention may be synthesized without template, and may be obtained from various commercial suppliers (e.g. Genscript Corporation).

In one embodiment, the nucleic acid constructs are naked DNA constructs comprising sequences encoding the dual agonist peptide.

Delivery Vehicles

It is also an aspect to provide the nucleic acid construct as described herein above comprised within a delivery vehicle. A delivery vehicle is an entity whereby a nucleotide sequence or polypeptide or both can be transported from at least one media to another. Delivery vehicles are generally used for expression of the sequences encoded within the nucleic acid construct and/or for the intracellular delivery of the construct or the polypeptide encoded therein.

In one embodiment, there is provided a delivery vehicle comprising the nucleic acid construct as defined herein. A delivery vehicle may be selected from the group consisting of: RNA based vehicles, DNA based vehicles/vectors, lipid based vehicles (such as a liposome), polymer based vehicles (such as a cationic polymer DNA carrier), colloidal gold particles (coating) and virally derived DNA or RNA vehicles or vectors.

Methods of non-viral delivery include physical (carrier-free delivery) and chemical approaches (synthetic vector-based delivery).

Physical approaches, including needle injection, gene gun, jet injection, electroporation, ultrasound, and hydrodynamic delivery, employ a physical force that permeates the cell membrane and facilitates intracellular gene transfer. Said physical force may be electrical or mechanical.

Examples of chemical delivery vehicles include, but are not limited to: biodegradable polymer microspheres, lipid based formulations such as liposome carriers, cationically charged molecules such as liposomes, calcium salts or dendrimers, lipopolysaccharides, polypeptides and polysaccharides.

Another embodiment comprises a vector which herein is denoted a viral vector (i.e. not a virus) as a delivery vehicle. Viral vectors according to the present invention are made from a modified viral genome, i.e. the actual DNA or RNA forming the viral genome, and introduced in naked form. Thus, any coat structures surrounding the viral genome made from viral or non-viral proteins are not part of the viral vector.

The virus from which the viral vector is derived may be selected from the non-exhaustive group of: adenoviruses, retroviruses, lentiviruses, adeno-associated viruses, herpesviruses, vaccinia viruses, foamy viruses, cytomegaloviruses, Semliki forest virus, poxviruses, RNA virus vector and DNA virus vector. Such viral vectors are well known in the art.

In one embodiment, said viral vectors may be selected from the group consisting of adenoviruses, lentiviruses, adeno-associated viruses (AAV) and recombinant adeno-associated viruses (rAAV). In one preferred embodiment, said viral vector is a therapeutic rAAV vector such as a therapeutic rAAV vector.

An adenovirus is a group of double-stranded DNA containing viruses. Adenoviruses can be genetically modified making them replication incompetent or conditionally replication incompetent. In this form, as adenoviral constructs or adenovectors, they can be used as gene delivery vehicles for vaccination or gene therapy.

Recombinant Cell

Another aspect of relates to a cell comprising the nucleic acid construct as defined herein. Such a recombinant cell can be used a tool for in vitro research, as a delivery vehicle for the nucleic acid construct or as part of a gene-therapy regime. The nucleic acid construct can be introduced into cells by techniques well known in the art which include microinjection of DNA into the nucleus of a cell, transfection, electroporation, lipofection/liposome fusion and particle bombardment. Suitable cells include autologous and non-autologous cells, and may include xenogenic cells.

Method of Preparation (Peptide)

The dual agonist peptides as defined herein may be prepared by any methods known in the art; such as by standard peptide-preparation techniques including solution synthesis or Merrifield-type solid phase synthesis.

In one embodiment a peptide according to the invention is synthetically made or produced. The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

In one embodiment the peptide or peptide sequences of the invention are produced synthetically, in particular, by the Sequence Assisted Peptide Synthesis (SAPS) method, by solution synthesis, by Solid-phase peptide synthesis (SPPS) such as Merrifield-type solid phase synthesis, by recombinant techniques (production by host cells comprising a first nucleic acid sequence encoding the peptide operably associated with a second nucleic acid capable of directing expression in said host cells) or enzymatic synthesis. These are well-known to the skilled person.

Peptides may be synthesised either batch-wise on a fully automated peptide synthesiser using 9-fluorenylmethyloxycarbonyl (Fmoc) or tert-Butyloxycarbonyl (Boc) as N-a-amino protecting group and suitable common protection groups for side-chain functionalities.

After purification such as by reversed phase HPLC, peptides may be further processed to obtain for example cyclic or C- or N-terminal modified isoforms. The methods for cyclization and terminal modification are well-known in the art.

For example, the following methods for conjugation of fatty acid can be used. After the last N-terminal N-Fmoc is removed, the N-terminal amino group is acylated by the treatment of 3 equiv 1,16-Hexadecanedioic acid in the presence of 3 equiv HATU and 6 equiv DI PEA. As an alternative, Lysine with Dde protected side chain is used for the solid phase peptide synthesis in the acylation position. After the peptide chain is assembled, the N-terminal amino group is capped by 3 equiv Boc2O in the presence of 6 equiv DIPEA. Then the protection group Dde is removed by the treatment of 2% hydrazine/DMF (v/v). As an alternative, 3 equiv palmitoyl chloride can be used for palmitoylation in the presence of 6 equiv DIPEA. Or 3 equiv 1,16-Hexadecanedioic acid can be activated by HATU/DI PEA and then conjugated to the side chain of Lysine. As a further alternative, Fmoc-γ-Glu(tBu)-OH or Fmoc-4-Abu-OH or Fmoc-β-Ala-OH or Fmoc-AEEAc-OH are conjugated to the side chain of Lys using a standard protocol of DIC/HOBT. The N-terminal amino groups of unnatural amino acids is then palmitoylated by the treatment of 3 equiv palmitoyl chloride in the presence of 6 equiv DIPEA.

Pharmaceutical Composition and Formulation

Whilst it is possible for the dual agonist peptide as defined herewith to be administered as the raw chemical (peptide), it is sometimes preferred to present them in the form of a pharmaceutical formulation. Such a pharmaceutical formulation may be referred to as a pharmaceutical composition, pharmaceutically acceptable composition or pharmaceutically safe composition.

Accordingly, also provided is a pharmaceutical formulation, which comprises a dual agonist peptide as defined herein, or a nucleic acid encoding the same, or a pharmaceutically acceptable salt or ester thereof, and a pharmaceutically acceptable carrier, excipient and/or diluent. The pharmaceutical formulations may be prepared by conventional techniques, e.g. as described in Remington: The Science and Practice of Pharmacy 2005, Lippincott, Williams & Wilkins.

Pharmaceutically acceptable salts of the instant peptide compounds, where they can be prepared, are also intended to be covered. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The peptide compounds may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

The pharmaceutically acceptable salt of the peptide of the invention is preferably in solution with a physiologically acceptable pH, i.e. the solution comprising the peptide salt preferably has a pH acceptable for clinical use.

Provided herewith is a composition comprising a peptide dual agonist as defined herein; or a multimeric compound comprising said peptide dual agonist; or a nucleic acid construct comprising/encoding said peptide dual agonist.

Administration and Dosage

In one embodiment of the present disclosure, a peptide or a nucleic acid construct encoding said peptide, or a composition comprising a peptide as defined herein is administered to individuals in need of treatment in pharmaceutically effective doses or a therapeutically effective amount. The dosage requirements will vary with the particular drug composition employed, the route of administration and the particular subject being treated, which depend on the severity and the sort of the disorder as well as on the weight and general state of the subject. It will also be recognized by one skilled in the art that the optimal quantity and spacing of individual dosages will be determined by the nature and extent of the condition being treated, the form, route and site of administration, and the particular patient being treated, and that such optima can be determined by conventional techniques.

It will also be appreciated by one of skill in the art that the optimal course of treatment, i.e., the number of doses of a compound given per day for a defined number of days, can be ascertained using conventional course of treatment determination tests.

In one embodiment the peptide or composition is administered at least once daily, such as once daily, such as twice daily, such as thrice daily, such as four times daily, such as five times daily.

A dose may also be administered in intermittent intervals, or intervals, whereby a dose is not administered every day. Rather one or more doses may be administered every second day, every third day, every fourth day, every fifth day, every sixth day, every week, every second week, every third week, every fourth week, every fifth week, every sixth week, or intervals within those ranges (such as every 2 to 4 weeks, or 4 to 6 weeks).

The skilled person knows that if the number of daily administrations is increased, the dose to be administered in each administration may be decreased accordingly. Likewise, if the duration of each administration is decreased, the dosage may be increased accordingly.

Routes of Administration

It will be appreciated that the preferred route of administration will depend on the general condition and age of the subject to be treated, the nature of the condition to be treated, the location of the tissue to be treated in the body and the active ingredient chosen.

Systemic Treatment

For systemic treatment the route of administration is capable of introducing the peptide, nucleic acid construct encoding said peptide, or the composition comprising the peptide into the blood stream to ultimately target the sites of desired action.

Such routes of administration are any suitable routes, such as an enteral route (including the oral, rectal, nasal, pulmonary, buccal, sublingual, transdermal, intracisternal and intraperitoneal administration), and/or a parenteral route (including subcutaneous, intramuscular, intrathecal, intracerebral, intravenous and intradermal administration).

Parenteral Administration

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration or subcutaneous administration. Furthermore, parenteral administration includes inhalations and topical administration.

Accordingly, compound be administered topically to cross any mucosal membrane of an animal to which the biologically active substance is to be given, e.g. in the nose, vagina, eye, mouth, genital tract, lungs, gastrointestinal tract, or rectum, preferably the mucosa of the nose, or mouth, and accordingly, parenteral administration may also include buccal, sublingual, nasal, rectal, vaginal and intraperitoneal administration as well as pulmonal and bronchial administration by inhalation or installation. Also, the agent may be administered topically to cross the skin.

Local Treatment

The peptide, or a nucleic acid construct encoding said peptide, or a composition comprising a peptide as defined herein may in one embodiment be used as a local treatment, i.e. be introduced directly to the site(s) of action. Accordingly, it may be applied to the skin or mucosa directly, or it may be injected into the site of action, for example into the diseased tissue or to an end artery leading directly to the diseased tissue.

Kit-of-Parts

The present invention also relates to a kit-of-parts comprising one or more of the agents described above (a peptide, a nucleic acid construct or a composition), and at least one additional or further component.

A kit of parts in one embodiment comprises one or more of the agents as defined herein for treatment, prevention or alleviation of a bone disorder osteoporosis and osteopenia. Kits as defined herein allows for simultaneous, sequential or separate administration of the active agent according to the present invention and/or one or more second active ingredients as described herein elsewhere.

```
Sequences
Co-1:
                                        (SEQ ID NO: 1)
HAEGTFISDYSTILDNLAARDFINWLIQTKITD Co-2:
                                        (SEQ ID NO: 2)
HAEGTFISDYSTILDNLAARDFINWLIQTKITD

NDWKHNITQ

Co-3:
                                        (SEQ ID NO: 3)
HADGTFISDYSTILDNLAARDFINWLIQTKITD

Co-4:
                                        (SEQ ID NO: 4)
HAEGSFISDYSTILDNLAARDFINWLIQTKITD

Co-5:
                                        (SEQ ID NO: 5)
HAEGTFSDEYSTILDNLAARDFINWLIQTKITD

Co-6:
                                        (SEQ ID NO: 6)
HAEGTFISDMNTILDNLAARDFINWLIQTKITD

Co-7:
                                        (SEQ ID NO: 7)
HAEGTFISDYSIAMDKLAARDFINWLIQTKITD

Co-8:
                                        (SEQ ID NO: 8)
HAEGTFISDYSTILDNIHQQDFINWLIQTKITD

Co-9:
                                        (SEQ ID NO: 9)
HAEGTFISDYSTILDNLAARDFVNWLLAQKITD

Co-10:
                                        (SEQ ID NO: 10)
HAEGTFISDYSTILDNLAARDFINWLIQTKGKK

Co-11:
                                        (SEQ ID NO: 11)
HGDGTFISDYSTILDNLAARDFINWLIQTKITD

Co-12:
                                        (SEQ ID NO: 12)
HVDGTFISDYSTILDNLAARDFINWLIQTKITD

Co-13:
                                        (SEQ ID NO: 13)
HADGTFSSDYSTILDNLAARDFINWLIQTKITD

Co-14:
                                        (SEQ ID NO: 14)
HADGTFIDDYSTILDNLAARDFINWLIQTKITD
```

Co-15:
(SEQ ID NO: 15)
HADGTFISEYSTILDNLAARDFINWLIQTKITD

Co-16:
(SEQ ID NO: 16)
HADGTFISDYSTILDNLAARDFINWLIQTKGTD

Co-17:
(SEQ ID NO: 17)
HADGTFISDYSTILDNLAARDFINWLIQTKIKD

Co-18:
(SEQ ID NO: 18)
HADGTFISDYSTILDNLAARDFINWLIQTKITK

Co-19:
(SEQ ID NO: 19)
HADGTFISDYSTILDNLAARDFINWLIQTKGKK

Consensus peptide 1:
(SEQ ID NO: 20)
HX1X2GX3FX4X5X6X7X8X9X10X11DX12LA

ARDFX13NWLX14X15X16KX17X18X19

Consensus peptide 2:
(SEQ ID NO: 21)
HX20X21GTFISDYSTILDNLAARDFX22NWL

X23X24X25KX26X27X28 hGIP:
(SEQ ID NO: 22)
YAEGTFISDYSIAMDKIHQQDFVNWLLAQKGK

KNDWKHNITQ hGLP-2:
(SEQ ID NO: 23)
HADGSFSDEMNTILDNLAARDFINWLIQTKITD

Consensus peptide 3:
(SEQ ID NO: 24)
HX29DGTFISDYSTILDNLAARDFINWLIQTKITD

C-terminus:
(SEQ ID NO: 25)
NDWKHNITQ

Co-20:
(SEQ ID NO: 26)
HADGTFSSDYSTILDNLAAKDFINWLIQTKITD

Co-24:
(SEQ ID NO: 27)
HADGTFISDYSKILDNLAARDFINWLIQTKITK

Co-25:
(SEQ ID NO: 28)
HADGTFISDYSTIKDNLAARDFINWLIQTKITK

Co-26:
(SEQ ID NO: 29)
HADGTFISDYSTILDKLAARDFINWLIQTKITK

Co-27:
(SEQ ID NO: 30)
HADGTFISDYSTILDNLKARDFINWLIQTKITK

Co-28:
(SEQ ID NO: 31)
HADGTFISDYSTILDNLAAKDFINWLIQTKITK

Co-34:
(SEQ ID NO: 32)
HADGTFISDYSTILDNLAARDFINWLIQTKGKKN

DWKHNITQ

Consensus peptide 4:
(SEQ ID NO: 33)
HX1X2GX3FX4X5X6X7X8X30X10X31DX12

LX32AX33DFX13NWLX14X15X16KX17X18X19

EXAMPLES

Example 1

Materials and Methods

Materials

Human native GIP(1-42) was purchased from Bachem™, Bubendorf, Switzerland (H5645) and human native GLP-2 was purchased from PolyPeptide. GIP-GLP-2 co-agonist 1-19 were designed based on identified structural elements important for activation of each receptor and synthesized by Caslo™, Lyngby, Denmark. cDNA of the human GIP and GLP-2 receptor was purchased from Origene (SC110906) and cloned into the pCMV-Script vector.

Transfections and Tissue Culture

COS-7 cells were cultured at 10% $CO_2$ and 37° C. in Dulbecco's modified Eagle's medium 1885 supplemented with 10% fetal bovine serum, 2 mM glutamine, 180 units/ml penicillin, and 45 g/ml streptomycin. Transient transfection of the COS-7 cells for cAMP accumulation was performed using the calcium phosphate precipitation method with the addition of chloroquine (Kissow et al., 2012).

cAMP Assay

In white 96-well plates transient transfected COS-7 expressing either the human GIP or GLP-2 receptor cells were seeded out in a density of $3,5*10^4$/well. The day after, the cells were washed twice with Hepes buffered saline (HBS) buffer and incubated with HBS and 1 mM 3-isobutyl-1-methylxanthine (IBMX) for 30 min at 37° C. Ligands were added and incubated for 30 min at 37° C. The Hit-Hunter™ cAMP XS assay (DiscoveRx) was carried out according to the manufacturer's instructions.

Results

GIP-GLP-2 co-agonists which are full agonists on both the human GIP and GLP-2 receptor were designed. First generation of GIP-GLP-2 co-agonist (co-1 and 2) were based on structural elements identified as being important for receptor activation of both the GIP receptor and GLP-2 receptor. The two following generations of co-agonists were based on knowledge acquired from the previous generation.

First Generation: Co-Agonist 1 and 2

Co-1:
(SEQ ID NO: 1)
HAEGTFISDYSTILDNLAARDFINWLIQTKITD

Co-2:
(SEQ ID NO: 2)
HAEGTFISDYSTILDNLAARDFINWLIQTKITDNDWKHNITQ

Second Generation: Co-Agonists 3-10

Co-3:
(SEQ ID NO: 3)
HADGTFISDYSTILDNLAARDFINWLIQTKITD

Co-4:
(SEQ ID NO: 4)
HAEGSFISDYSTILDNLAARDFINWLIQTKITD

Co-5:
(SEQ ID NO: 5)
HAEGTFSDEYSTILDNLAARDFINWLIQTKITD

Co-6:
(SEQ ID NO: 6)
HAEGTFISDMNTILDNLAARDFINWLIQTKITD

Co-7:
(SEQ ID NO: 7)
HAEGTFISDYSIAMDKLAARDFINWLIQTKITD

Co-8:
(SEQ ID NO: 8)
HAEGTFISDYSTILDNIHQQDFINWLIQTKITD

Co-9:
(SEQ ID NO: 9)
HAEGTFISDYSTILDNLAARDFVNWLLAQKITD

Co-10:
(SEQ ID NO: 10)
HAEGTFISDYSTILDNLAARDFINWLIQTKGKK

Third Generation: Co-Agonists 11-19:

Modifications of positions 2, 7, 8, 9, 31, 32, 33 in the sequence of co-agonist 3 (SEQ ID NO:3) were introduced. G and V were inserted at position 2 to potentially increase half-life time of the peptide in vivo.

Co-11:
(SEQ ID NO: 11)
HGDGTFISDYSTILDNLAARDFINWLIQTKITD

Co-12:
(SEQ ID NO: 12)
HVDGTFISDYSTILDNLAARDFINWLIQTKITD

Co-13:
(SEQ ID NO: 13)
HADGTFSSDYSTILDNLAARDFINWLIQTKITD

Co-14:
(SEQ ID NO: 14)
HADGTFIDDYSTILDNLAARDFINWLIQTKITD

Co-15:
(SEQ ID NO: 15)
HADGTFISEYSTILDNLAARDFINWLIQTKITD

Co-16:
(SEQ ID NO: 16)
HADGTFISDYSTILDNLAARDFINWLIQTKGTD

Co-17:
(SEQ ID NO: 17)
HADGTFISDYSTILDNLAARDFINWLIQTKIKD

Co-18:
(SEQ ID NO: 18)
HADGTFISDYSTILDNLAARDFINWLIQTKITK

Co-19:
(SEQ ID NO: 19)
HADGTFISDYSTILDNLAARDFINWLIQTKGKK

As shown in Table 1 herein below, co-agonist 3 activates the GIP receptor with the same potency as native GIP(1-42). Co-agonists 1-19 show an increased potency on both the GIP and GLP-2 receptor ranging from 2.8 to 5124 and 4.4 to 293 fold increases, respectively. Importantly, both co-agonist 18 and 19 had almost the same potency and efficacy on the GIPR and GLP-2R as native GIP and GLP-2, respectively.

TABLE 1

The table displays the $EC_{50}$-values (both log and nM values) of co-agonist 1-19 from the cAMP studies with fold change of native GIP or GLP-2 on the GIP receptor and the GLP-2 receptor, respectively. In addition, the efficacy ($E_{max}$ values) is written as percent activation compared to native GIP and GLP-2 on the GIP and GLP-2 receptor, respectively.

| Ligand | GIP receptor | | | | GLP-2 receptor | | | |
|---|---|---|---|---|---|---|---|---|
| | $logEC_{50}$ | $EC_{50}$(nM) | fold | Emax (10 µM) | $logEC_{50}$ | $EC_{50}$(nM) | fold | Emax (10 µM) |
| GIP | −10.05 | 0.089 | 1 | 100% | no activation | | | |
| GLP-2 | −7.25 | 56 | — | 22% | −8.94 | 1.2 | 1 | 100% |
| Co-agonist 1 | −7.53 | 30 | 337 | 1 µM: 100% | −7.01 | 98 | 82 | 1 µM: 93% |
| Co-agonist 2 | −7.92 | 12 | 135 | 1 µM: 100% | −6.84 | 145 | 121 | 1 µM: 93% |
| Co-agonist 3 | −9.97 | 0.11 | 1.2 | 100% | −7.67 | 21 | 18 | 100% |
| Co-agonist 4 | −7.42 | 38 | 427 | 83% | −7.59 | 25 | 21 | 90% |
| Co-agonist 5 | −6.34 | 456 | 5124 | 75% | −8.21 | 6.2 | 5.2 | 91% |
| Co-agonist 6 | −6.77 | 172 | 1933 | 83% | −7.22 | 60 | 50 | 70% |
| Co-agonist 7 | −7.59 | 26 | 292 | 92% | −6.45 | 351 | 293 | 78% |
| Co-agonist 8 | −8.23 | 5.9 | 66 | 100% | >−5.00 | — | — | 22% |
| Co-agonist 9 | −8.50 | 3.2 | 36 | 100% | −6.91 | 123 | 103 | 67% |
| Co-agonist 10 | −8.27 | 5.4 | 61 | 100% | −7.66 | 22 | 18 | 77% |
| Co-agonist 11 | −8.50 | 3.2 | 36 | 95% | −7.62 | 24 | 20 | 87% |
| Co-agonist 12 | −8.96 | 1.1 | 12 | 96% | −7.60 | 25 | 21 | 81% |
| Co-agonist 13 | −7.92 | 12 | 135 | 91% | −7.95 | 11 | 9.2 | 99% |
| Co-agonist 14 | −8.63 | 2.4 | 27 | 94% | −7.97 | 11 | 9.2 | 90% |

TABLE 1-continued

The table displays the $EC_{50}$-values (both log and nM values) of co-agonist 1-19 from the cAMP studies with fold change of native GIP or GLP-2 on the GIP receptor and the GLP-2 receptor, respectively. In addition, the efficacy ($E_{max}$ values) is written as percent activation compared to native GIP and GLP-2 on the GIP and GLP-2 receptor, respectively.

| Ligand | GIP receptor | | | | GLP-2 receptor | | | |
|---|---|---|---|---|---|---|---|---|
| | $logEC_{50}$ | $EC_{50}$(nM) | fold | Emax (10 μM) | $logEC_{50}$ | $EC_{50}$(nM) | fold | Emax (10 μM) |
| Co-agonist 15 | −8.50 | 3.2 | 36 | 92% | −8.18 | 6.7 | 5.6 | 104% |
| Co-agonist 16 | −9.22 | 0.60 | 6.7 | 95% | −7.06 | 82 | 68 | 74% |
| Co-agonist 17 | −9.39 | 0.40 | 4.5 | 95% | −7.61 | 25 | 21 | 88% |
| Co-agonist 18 | −9.18 | 0.66 | 7.4 | 89% | −8.28 | 5.3 | 4.4 | 94% |
| Co-agonist 19 | −9.60 | 0.25 | 2.8 | 93% | −8.14 | 7.2 | 6 | 91% |

Example 2

The methodology described in Example 1 was followed to test fourth generation co-agonists.

Fourth Generation: Co-Agonists 20, 24-28 and 34:

Modification of position 20 in the sequence of co-agonist 13 (SEQ ID NO: 13) was introduced to generate co-agonist 20. Modifications in positions 12, 14, 16, 18 and 20 in the sequence of co-agonist 18 (SEQ ID NO: 13) were introduced to generate co-agonists 24, 25, 26, 27 and 28, respectively. The 9 C-terminal amino acids of hGIP were added to the sequence of co-agonist 19 to generate co-agonist 34. C-12 or C-16 acyl groups were added on position 1, 20, 30, 32 or 33 of the sequence of co-agonists 13, 20 18 and 19 so to increase the co-agonists half-life. Co-agonists 21-23, 29-33, 35 and 36 were so generated.

```
Co-20:
                              (SEQ ID NO: 26)
HADGTFSSDYSTILDNLAAKDFINWLIQTKITD

Co-21:
                              SEQ ID NO: 26
HADGTFSSDYSTILDNLAAK(C16/20)DFINWLIQTKITD
with C16 pos 20

Co-22:
                              SEQ ID NO: 13
H(C16/1)ADGTFSSDYSTILDNLAARDFINWLIQTKITD
with C16 pos 1

Co-23:
                              SEQ ID NO: 13
HADGTFSSDYSTILDNLAARDFINWLIQTK(C16/30)ITD
with C16 pos 30

Co-24:
                              (SEQ ID NO: 27)
HADGTFISDYSKILDNLAARDFINWLIQTKITK

Co-25:
                              (SEQ ID NO: 28)
HADGTFISDYSTIKDNLAARDFINWLIQTKITK

Co-26:
                              (SEQ ID NO: 29)
HADGTFISDYSTILDKLAARDFINWLIQTKITK

Co-27:
                              (SEQ ID NO: 30)
HADGTFISDYSTILDNLKARDFINWLIQTKITK

Co-28:
                              (SEQ ID NO: 31)
HADGTFISDYSTILDNLAAKDFINWLIQTKITK

Co-29:
                              SEQ ID NO: 18
H(C16/1)ADGTFISDYSTILDNLAARDFINWLIQTKITK
with C16 pos 1

Co-30:
                              SEQ ID NO: 18
HADGTFISDYSTILDNLAARDFINWLIQTK(C12/30)ITK
with C12 pos 30

Co-31:
                              SEQ ID NO: 18
HADGTFISDYSTILDNLAARDFINWLIQTK(C16/30)ITK
with C16 pos 30

Co-32:
                              SEQ ID NO: 18
HADGTFISDYSTILDNLAARDFINWLIQTKITK(C12/33)
with C12 pos 33

Co-33:
                              SEQ ID NO: 18
HADGTFISDYSTILDNLAARDFINWLIQTKITK(c16/33)
with C16 pos 33

Co-34:
                              (SEQ ID NO: 32)
HADGTFISDYSTILDNLAARDFINWLIQTKGKKNDWKHNITQ

Co-35:
                              SEQ ID NO: 19
HADGTFISDYSTILDNLAARDFINWLIQTKGK(C12/32)K
with C12 pos 32

Co-36:
                              SEQ ID NO: 19
HADGTFISDYSTILDNLAARDFINWLIQTKGK(C16/32)K
with C16 pos 32
```

TABLE 2

$EC_{50}$-values (log and nM values) of co-agonist 20-36 from the cAMP studies with fold change of native GIP or GLP-2 on the GIP receptor and the GLP-2 receptor, respectively. In addition, the efficacy ($E_{max}$ values) is written as percent activation compared to native GIP and GLP-2 on the GIP and GLP-2 receptor, respectively.

| | GIP receptor | | | | GLP-2 receptor | | | |
|---|---|---|---|---|---|---|---|---|
| Ligand | $logEC_{50}$ | $EC_{50}$(nM) | fold | Emax (10 µM) | $logEC_{50}$ | $EC_{50}$(nM) | fold | Emax (10 µM) |
| GIP | −10.05 | 0.089 | 1 | 100% | no activation | | | |
| GLP-2 | −7.25 | 56 | — | 22% | −8.94 | 1.2 | 1 | 100% |
| Co-agonist 20 | −9.23 | 0.59 | 6.6 | 98% | −8.92 | 1.2 | 1.0 | 80% |
| Co-agonist 21 | −7.47 | 34 | 381 | 94% | −8.22 | 6.0 | 5.0 | 75% |
| Co-agonist 22 | −9.39 | 0.41 | 4.6 | 100% | −8.88 | 1.3 | 1.1 | 72% |
| Co-agonist 23 | −9.12 | 0.76 | 8.5 | 81% | −8.85 | 1.4 | 1.2 | 57% |
| Co-agonist 24 | −9.82 | 0.15 | 1.7 | 100% | −9.13 | 0.74 | 0.62 | 96% |
| Co-agonist 25 | −9.36 | 0.44 | 4.9 | 92% | −8.46 | 3.5 | 2.9 | 92% |
| Co-agonist 26 | −10.52 | 0.03 | 0.34 | 100% | −9.51 | 0.31 | 0.26 | 100% |
| Co-agonist 27 | −9.26 | 0.55 | 6.2 | 100% | −9.25 | 0.56 | 0.47 | 100% |
| Co-agonist 28 | −9.70 | 0.20 | 2.2 | 100% | −8.93 | 1.2 | 0.98 | 112% |
| Co-agonist 29 | −8.74 | 1.82 | 20 | 115% | −7.76 | 17 | 14 | 82% |
| Co-agonist 30 | −9.20 | 0.63 | 7.1 | 100% | −7.44 | 36 | 30 | 73% |
| Co-agonist 31 | −8.77 | 1.70 | 19 | 91% | -6.97 | 107 | 89 | 91% |
| Co-agonist 32 | −9.81 | 0.15 | 1.7 | 100% | −8.21 | 6.2 | 5.1 | 91% |
| Co-agonist 33 | −9.50 | 0.32 | 3.6 | 100% | −7.89 | 13 | 11 | 82% |
| Co-agonist 34 | −10.0 | 0.10 | 1.1 | 100% | −8.94 | 1.2 | 0.96 | 94% |
| Co-agonist 35 | −9.32 | 0.48 | 5.4 | 99% | −8.63 | 2.3 | 1.9 | 68% |
| Co-agonist 36 | −9.10 | 0.79 | 8.9 | 100% | −7.70 | 20 | 17 | 71% |

Example 3

Human study 1

Aim: Investigating the effect of subcutaneously administered native GIP and GLP-2 on bone remodelling.

Method: Eight healthy young men were enrolled. The study included three study days in randomised order (with a minimum of 1 week washout between study days) where human GIP (200 µg), human GLP-2 (800 µg), or placebo was injected subcutaneously. Participants arrived in the morning (fasted overnight) and received the injection around 8.30 a.m. Blood samples were collected before (−25 and −10 min) and every 30 minutes after injection (30, 60, 90, 120, 180 and 240 min). After last participant's last visit, bone resorption was determined by measurements of serum C-terminal cross-linking telopeptide of type I collagen (CTX; IDS Immunodiagnostic Systems GmbH, Frankfurt am Main, Germany)

Results: GIP (200 µg) and GLP-2 (800 µg) both inhibited bone resorption as measured by plasma CTX concentration. The maximum effect of GIP was seen 90 min after injection where bone resorption was reduced to 56.2±11.2% of base line. The maximum effect of GLP-2, down to 63.4±3.4% of base line was reached 180 min after administration (FIG. 1).

Conclusion: These results show that administration of GIP and GLP-2 both inhibited bone resorption; furthermore a subcutaneous injection of GIP results in a marked reduction in bone resorption.

Example 4

Human Study 2

Aim: Proof of concept study investigating the synergistic effect of native GIP and GLP-2 on bone resorption by comparing the effects achieved when the hormones are administered alone with the effect reached when they are administered together.

Method: Ten healthy young men are enrolled and the study includes four study days in randomised order (with a minimum of 1 week washout between study days) where human GIP (100 µg), human GLP-2 (400 µg), GIP+GLP-2 (100 µg+400 µg), or placebo are injected subcutaneously. The participants arrive in the morning (fasted overnight) and receive the injection around 8.30 a.m. Blood samples are collected before (−25 and −10) and every 30 minutes after injection (30, 60, 90, 120, 180 and 240 min) injection. After last participant's last visit, samples are analysed for concentrations of bone resorption markers (CTX). The doses of GIP and GLP-2 have been selected based on Example 1 showing pronounced (~50%) reduction in bone resorption (CTX) which is comparable to the reduction seen after meal ingestion (which is believed to be the maximal achievable) using 200 μg GIP and 800 μg GLP-2. To be able to measure a synergistic/additive effect we have, therefore, reduced the doses in Example 3.

Figure 2:
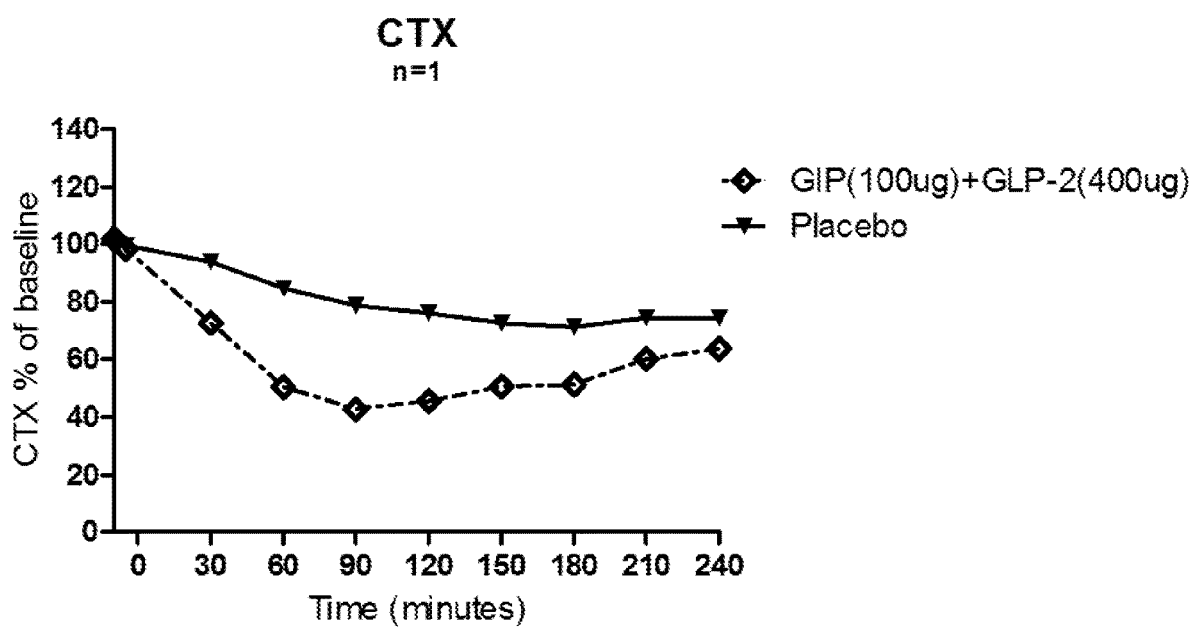
FIG. 2: Measurements of serum C-terminal cross-linking telopeptide of type I collagen (CTX) in blood samples collected at 30 minutes interval after injection of hGLP-2 and hGIP, or placebo (cf. Example 4)

Results: The combination of GIP and GLP-2 induced a pronounced reduction in bone resorption. The maximum effect was seen 90 min after injection where the bone resorption was reduced with approximately 60% (down to 42.8% of base line) (FIG. 2).

Conclusion: These results show that subcutaneous administration of GIP and GLP-2 together has a synergistic effect on reducing bone resorption.

Example 5

Aim: Testing the effects of 2 test compounds on differentiation and activity of osteoblasts in vitro in a preliminary set-up.

Method: One concentration of each test compound (1 μM) is tested. Effects on osteoblast differentiation are studied using a mouse mesenchymal osteoblast precursor cell line KS483. The cells are cultured on plastic surface in 96-well plates for 8 days, allowing them to differentiate into mature bone-forming osteoblasts. Baseline with vehicle
1. Compound 3: Vehicle
2. Compound 5: GIP-GLP-2 agonist 3 (SEQ ID NO:3)
3. Compound 6: GIP-GLP-2 agonist 19 (SEQ ID NO:19)

In osteoblast differentiation assay: Intracellular alkaline phosphatase activity (ALP) at day 8 as an index of the number of mature osteoblasts formed.

Figure 3:
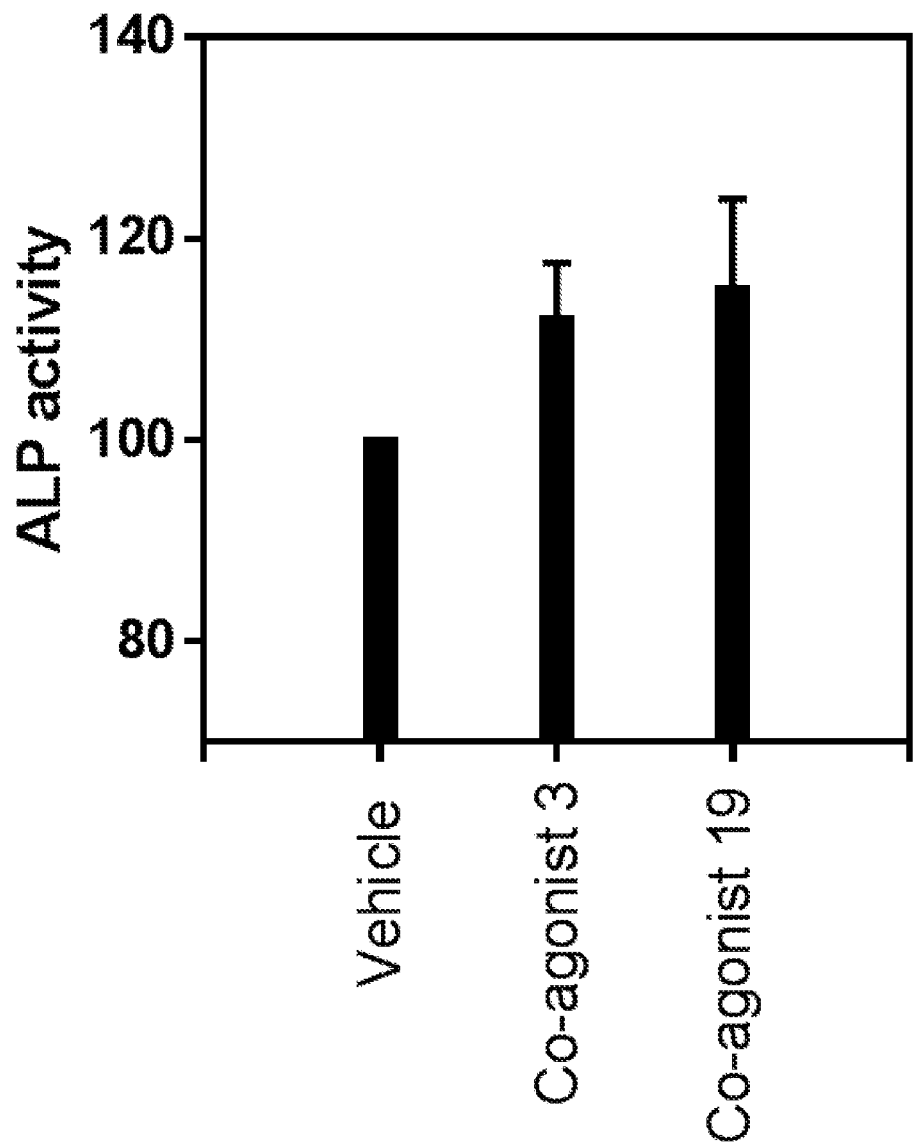
FIG. 3: Intracellular alkaline phosphatase activity (ALP) at 8 days of culturing mouse mesenchymal osteoblast precursor cell line KS483 with vehicle, GIP-GLP-2 agonist 3 (SEQ ID NO:3) or GIP-GLP-2 agonist 19 (SEQ ID NO:19) (cf. Example 5).

Results: Both GIP-GLP-2 agonist 3 (SEQ ID NO:3) and GIP-GLP-2 agonist 19 (SEQ ID NO:19) resulted in increased ALP activity. At day 8 the ALP activity was 112±5.6% in the agonist 3 treated and 115±8.9% in the agonist 19 treated compared to vehicle (mean±sem; n=6) (FIG. 3).

Conclusion: This in vitro study verifies that the co-agonist increases the number of mature osteoblasts as measured by increased concentration of ALP.

The invention claimed is:

1. A peptide dual agonist of the GIPR (glucose-dependent insulinotropic polypeptide receptor) and of the GLP2R (glucagon-like peptide-2 receptor), said peptide comprising $$HX_{20}X_{21}GTFISDYSTILDNLAARDFX_{22}NWLX_{23}X_{24}X_{25}KX_{26}X_{27}X_{28},$$
(SEQ ID NO: 21)

where $X_{20}$ is selected from A, V and G,
$X_{21}$ is selected from D and E,
$X_{22}$ is selected from I and V,
$X_{23}$ is selected from I and L,
$X_{24}$ is selected from Q and A,
$X_{25}$ is selected from T and Q,
$X_{26}$ is selected from I and G,
$X_{27}$ is selected from T and K, and
$X_{28}$ is selected from D and K,
or a functional variant thereof having 1, 2, 3 or 4 individual amino acid substitutions, wherein said functional variant comprises substitution of 0, 1, or 2 of amino acids 5 to 11 of SEQ ID NO:21, wherein said functional variant binds to and activates the GIPR and the GLP-2R, and wherein said peptide:
  a) activates the GIPR with an efficacy ($E_{max}$ values) which is at least 65% of the efficacy by which native GIP activates the GIPR, and
  b) activates the GLP2R with an efficacy ($E_{max}$ values) which is at least 65% of the efficacy by which native GLP-2 activates the GLP2R.

2. The peptide dual agonist according to claim 1, wherein said peptide comprises a sequence selected from the group consisting of:

a)

HGDGTFISDYSTILDNLAARDFINWLIQTKITD, (SEQ ID NO: 11)

HADGTFSSDYSTILDNLAARDFINWLIQTKITD, (SEQ ID NO: 13)

and a functional variant of either thereof having 1 or 2 individual amino acid substitutions;

b)

HADGTFISDYSTILDNLAARDFINWLIQTKITD, (SEQ ID NO: 3)

HAEGSFISDYSTILDNLAARDFINWLIQTKITD, (SEQ ID NO: 4)

HAEGTGSDEYSTILDNLAARDFINWLIQTKITD, (SEQ ID NO: 5)

HAEGTFISDMNTILDNLAARDFINWLIQTKITD, (SEQ ID NO: 6)

HVDGTFISDYSTILDNLAARDFINWLIQTKITD, (SEQ ID NO: 12)

HADGTFIDDYSTILDNLAARDFINWLIQTKITD, (SEQ ID NO: 14)

-continued

```
                                         (SEQ ID NO: 15)
HADGTFISEYSTILDNLAARDFINWLIQTKITD, (SEQ ID NO: 26)
HADGTFSSDYSTILDNLAAKDFINWLIQTKITD,
``` and a functional variant of any thereof having 1 or 2 individual amino acid substitutions;

c)

```
                                         (SEQ ID NO: 1)
HAEGTFISDYSTILDNLAARDFINWLIQTKITD, (SEQ ID NO: 2)
HAEGTFISDYSTILDNLAARDFINWLIQTKITDNDWKHNITQ, (SEQ ID NO: 16)
HADGTFISDYSTILDNLAARDFINWLIQTKGTD, (SEQ ID NO: 17)
HADGTFISDYSTILDNLAARDFINWLIQTKIKD, (SEQ ID NO: 18)
HADGTFISDYSTILDNLAARDFINWLIQTKITK, (SEQ ID NO: 27)
HADGTFISDYSKILDNLAARDFINWLIQTKITK, (SEQ ID NO: 28)
HADGTFISDYSTIKDNLAARDFINWLIQTKITK, (SEQ ID NO: 29)
HADGTFISDYSTILDKLAARDFINWLIQTKITK, (SEQ ID NO: 30)
HADGTFISDYSTILDNLKARDFINWLIQTKITK, (SEQ ID NO: 31)
HADGTFISDYSTILDNLAAKDFINWLIQTKITK, (SEQ ID NO: 32)
HADGTFISDYSTILDNLAARDFINWLIQTKGKKNDWKHNITQ, (SEQ ID NO: 9)
HAEGTFISDYSTILDNLAARDFVNWLLAQKITD, (SEQ ID NO: 10)
HAEGTFISDYSTILDNLAARDFINWLIQTKGKK, (SEQ ID NO: 19)
HADGTFISDYSTILDNLAARDFINWLIQTKGKK,
``` and a functional variant of any thereof having 1, 2, or 3 individual amino acid substitutions;

d)

```
                                         (SEQ ID NO: 7)
HAEGTFISDYSIAMDKLAARDFINWLIQTKITD, (SEQ ID NO: 8)
HAEGTFISDYSTILDNIHQQDFINWLIQTKITD,
``` and a functional variant of either thereof having 1, 2, or 3 individual amino acid substitutions, wherein said functional variant of any of a), b), c) or d) comprises substitution of 0, 1, or 2 of amino acids 5 to 11 of SEQ ID NO:21, and wherein said functional variant binds to and activates the GIPR and the GLP-2R, and wherein said peptide:

a. activates the GIPR with an efficacy ($E_{max}$ values) which is at least 65% of the efficacy by which native GIP activates the GIPR, and b. activates the GLP2R with an efficacy ($E_{max}$ values) which is at least 65% of the efficacy by which native GLP-2 activates the GLP2R.

3. The peptide dual agonist according to claim 2, wherein said peptide is modified by attaching at least one fatty acid molecule at one or more amino acid residues of any one of SEQ ID NOs: 1-19 and 26-32.

4. The peptide dual agonist according to claim 3, wherein said peptide is modified by attaching at least one fatty acid molecule at one or more lysine residues.

5. The peptide dual agonist according to claim 3, wherein said fatty acid molecule is a monoacyl fatty acid molecule, comprising one fatty acid.

6. The peptide dual agonist according to claim 3, wherein said fatty acid molecule is a diacyl fatty acid molecule.

7. The peptide dual agonist according to claim 3, wherein said fatty acid molecule comprises an acyl group of the formula $CH_3(CH_2)_nCO$—, wherein n in an integer from 4 to 24.

8. The peptide dual agonist according to claim 7, wherein said fatty acid molecule comprises an acyl group selected from the group consisting of: $CH_3(CH_2)_{10}CO$— (lauryl, C12), $CH_3(CH_2)_{12}CO$— (myristoyl, C14), $CH_3(CH_2)_{14}O$— (palmitoyl, C16) and $CH_3(CH_2)_{16}CO$— (stearyl, C18).

9. The peptide dual agonist according to claim 3, said peptide comprising a peptide selected from the group consisting of:

```
                                         (SEQ ID NO: 18)
H(C16/1)ADGTFISDYSTILDNLAARDFINWLIQTKITK, (SEQ ID NO: 18)
HADGTFISDYSTILDNLAARDFINWLIQTK(C12/30)ITK, (SEQ ID NO: 18)
HADGTFISDYSTILDNLAARDFINWLIQTK(C16/30)ITK, (SEQ ID NO: 18)
HADGTFISDYSTILDNLAARDFINWLIQTKITK(C12/33), (SEQ ID NO: 18)
HADGTFISDYSTILDNLAARDFINWLIQTKITK(C16/33), (SEQ ID NO: 19)
HADGTFISDYSTILDNLAARDFINWLIQTKGK(C12/32)K, (SEQ ID NO: 19)
HADGTFISDYSTILDNLAARDFINWLIQTKGK(C16/32)K, (SEQ ID NO: 26)
HADGTFSSDYSTILDNLAAK(C16/20)DFINWLIQTKITD, (SEQ ID NO: 13)
H(C16/1)ADGTFSSDYSTILDNLAARDFINWLIQTKITD, (SEQ ID NO: 13)
HADGTFSSDYSTILDNLAARDFINWLIQTK(C16/30)ITD,
``` and a functional variant of any thereof having 1 or 2 individual amino acid substitutions, wherein said functional variant binds to and activates the GIPR and the GLP-2R.

10. The peptide dual agonist according to claim 1, wherein said peptide further comprises additional amino acids at the C-terminus.

11. The peptide dual agonist according to claim 10, wherein said additional amino acids comprises NDWKHNITQ (SEQ ID NO. 25), or a variant or fragment of SEQ ID NO:25.

12. The peptide dual agonist according to claim 1, wherein said peptide is C-terminally amidated (—NH$_2$) and/or wherein said peptide is N-terminally acetylated (COCH$_3$).

13. The peptide dual agonist according to claim 1, wherein said peptide
   a) binds to GIPR and GLP2R, and/or
   b) stimulates GIPR- and GLP2R-mediated cAMP production, and/or
   c) inhibits bone resorption, and/or
   d) stimulates bone formation.

14. The peptide dual agonist according to claim 1, wherein said peptide is capable of
   a) activating the GIPR with an efficacy (E$_{max}$ values) which is at least 70% of the efficacy by which native GIP activates the GIPR, and
   b) activating the GLP2R with an efficacy (E$_{max}$ values) which is at least 70% of the efficacy by which native GLP-2 activates the GLP2R.

15. A method of inhibiting bone resorption and stimulating bone formation comprising administering a therapeutically effective amount of a peptide dual agonist of the GIPR and of the GLP2R, said peptide comprising

HX$_{20}$X$_{21}$GTFISDYSTILDNLAARD

FX$_{22}$NWLX$_{23}$X$_{24}$X$_{25}$KX$_{26}$X$_{27}$X$_{28}$,    (SEQ ID NO: 21)

wherein X$_{20}$ is selected from A, V and G,
X$_{21}$ is selected from D and E,
X$_{22}$ is selected from I and V,
X$_{23}$ is selected from I and L,
X$_{24}$ is selected from Q and A,
X$_{25}$ is selected from T and Q,
X$_{26}$ is selected from I and G,
X$_{27}$ is selected from T and K, and
X$_{28}$ is selected from D and K,
   or a functional variant thereof having 1, 2, 3 or 4 individual amino acid substitutions,
   wherein said functional variant comprises substitution of 0, 1, or 2 of amino acids 5 to 11 of SEQ ID NO:21, and wherein said functional variant binds to and activates the GIPR and the GLP-2R, and wherein said peptide:
   a) activates the GIPR with an efficacy (E$_{max}$ values) which is at least 65% of the efficacy by which native GIP activates the GIPR, and
   b) activates the GLP2R with an efficacy (E$_{max}$ values) which is at least 65% of the efficacy by which native GLP-2 activates the GLP2R.

16. The method according to claim 15, wherein said peptide comprises a sequence selected from the group consisting of:

a)

HGDGTFISDYSTILDNLAARDFINWLIQTKITD,    (SEQ ID NO: 11)

HADGTFSSDYSTILDNLAARDFINWLIQTKITD,    (SEQ ID NO: 13)

and a functional variant of either thereof having 1 or 2 individual amino acid substitutions;

b)

HADGTFISDYSTILDNLAARDFINWLIQTKITD,    (SEQ ID NO: 3)

HAEGSFISDYSTILDNLAARDFINWLIQTKITD,    (SEQ ID NO: 4)

HAEGTFSDEYSTILDNLAARDFINWLIQTKITD,    (SEQ ID NO: 5)

HAEGTFISDMNTILDNLAARDFINWLIQTKITD,    (SEQ ID NO: 6)

HVDGTFISDYSTILDNLAARDFINWLIQTKITD,    (SEQ ID NO: 12)

HADGTFIDDYSTILDNLAARDFINWLIQTKITD,    (SEQ ID NO: 14)

HADGTFISEYSTILDNLAARDFINWLIQTKITD,    (SEQ ID NO: 15)

HADGTFSSDYSTILDNLAAKDFINWLIQTKITD,    (SEQ ID NO: 26)

and a functional variant of any thereof having 1 or 2 individual amino acid substitutions;

c)

HAEGTFISDYSTILDNLAARDFINWLIQTKITD,    (SEQ ID NO: 1)

HAEGTFISDYSTILDNLAARDFINWLIQTKITDNDWKHNITQ,    (SEQ ID NO: 2)

HADGTFISDYSTILDNLAARDFINWLIQTKGTD,    (SEQ ID NO: 16)

HADGTFISDYSTILDNLAARDFINWLIQTKIKD,    (SEQ ID NO: 17)

HADGTFISDYSTILDNLAARDFINWLIQTKITK,    (SEQ ID NO: 18)

HADGTFISDYSKILDNLAARDFINWLIQTKITK,    (SEQ ID NO: 27)

HADGTFISDYSTIKDNLAARDFINWLIQTKITK,    (SEQ ID NO: 28)

HADGTFISDYSTILDKLAARDFINWLIQTKITK,    (SEQ ID NO: 29)

HADGTFISDYSTILDNLKARDFINWLIQTKITK,    (SEQ ID NO: 30)

HADGTFISDYSTILDNLAAKDFINWLIQTKITK,    (SEQ ID NO: 31)

HADGTFISDYSTILDNLAARDFINWLIQTKGKKNDWKHNITQ,    (SEQ ID NO: 32)

HAEGTFISDYSTILDNLAARDFVNWLLAQKITD,    (SEQ ID NO: 9)

HAEGTFISDYSTILDNLAARDFINWLIQTKGKK,    (SEQ ID NO: 10)

HADGTFISDYSTILDNLAARDFINWLIQTKGKK,    (SEQ ID NO: 19)

and a functional variant of any thereof having 1, 2 or 3 individual amino acid substitutions;

d)

HAEGTFISDYSIAMDKLAARDFINWLIQTKITD, (SEQ ID NO: 7)

HAEGTFISDYSTILDNIHQQDFINWLIQTKITD, (SEQ ID NO: 8)

and a functional variant of any thereof having 1, 2, or 3 individual amino acid substitutions;
wherein said functional variant of any of a), b), c) or d) comprises substitution of 0, 1, or 2 of amino acids 5 to 11 of SEQ ID NO:21, and wherein said functional variant binds to and activates the GIPR and the GLP-2R, and wherein said peptide:
  a. activates the GIPR with an efficacy ($E_{max}$ values) which is at least 65% of the efficacy by which native GIP activates the GIPR, and
  b. activates the GLP2R with an efficacy ($E_{max}$ values) which is at least 65% of the efficacy by which native GLP-2 activates the GLP2R.

17. A method treating a bone disorder comprising administering a therapeutically effective amount of a peptide dual agonist of the GIPR and of the GLP2R, said peptide comprising the sequence HX$_{20}$X$_{21}$GTFISDYSTILDNLAARDF X$_{22}$NWLX$_{23}$X$_{24}$X$_{25}$KX$_{26}$X$_{27}$X$_{28}$, (SEQ ID NO: 21)

wherein X$_{20}$ is selected from A, V and G,
X$_{21}$ is selected from D and E,
X$_{22}$ is selected from I and V,
X$_{23}$ is selected from I and L,
X$_{24}$ is selected from Q and A,
X$_{25}$ is selected from T and Q,
X$_{26}$ is selected from I and G,
X$_{27}$ is selected from T and K, and
X$_{28}$ is selected from D and K,
or a functional variant thereof having 1, 2, 3 or 4 individual amino acid substitutions,
wherein said functional variant comprises substitution of 0, 1, or 2 of amino acids 5 to 11 of SEQ ID NO:21, and wherein said functional variant binds to and activates the GIPR and the GLP-2R, and wherein said peptide:
  a) activates the GIPR with an efficacy ($E_{max}$ values) which is at least 65% of the efficacy by which native GIP activates the GIPR, and
  b) activates the GLP2R with an efficacy ($E_{max}$ values) which is at least 65% of the efficacy by which native GLP-2 activates the GLP2R.

18. The method according to claim 17, wherein said bone disorder is selected from the group consisting of: osteopenia, osteoporosis, severe osteoporosis, osteomalacia, rickets, osteitis fibrosa cystica (OFC) and Paget's disease of bone.

19. The method according to claim 17, wherein said peptide comprises or consists of a sequence selected from the group consisting of:
a)

HGDGTFISDYSTILDNLAARDFINWLIQTKITD, (SEQ ID NO: 11)

HADGTFSSDYSTILDNLAARDFINWLIQTKITD, (SEQ ID NO: 13)

and a functional variant of either thereof having 1 or 2 individual amino acid substitutions;
b)

HADGTFISDYSTILDNLAARDFINWLIQTKITD, (SEQ ID NO: 3)

HAEGSFISDYSTILDNLAARDFINWLIQTKITD, (SEQ ID NO: 4)

HAEGTGSDEYSTILDNLAARDFINWLIQTKITD, (SEQ ID NO: 5)

HAEGTFISDMNTILDNLAARDFINWLIQTKITD, (SEQ ID NO: 6)

HVDGTFISDYSTILDNLAARDFINWLIQTKITD, (SEQ ID NO: 12)

HADGTFIDDYSTILDNLAARDFINWLIQTKITD, (SEQ ID NO: 14)

HADGTFISEYSTILDNLAARDFINWLIQTKITD, (SEQ ID NO: 15)

HADGTFSSDYSTILDNLAAKDFINWLIQTKITD, (SEQ ID NO: 26)

and a functional variant of any thereof having 1 or 2 individual amino acid substitutions;
c)

HAEGTFISDYSTILDNLAARDFINWLIQTKITD, (SEQ ID NO: 1)

HAEGTFISDYSTILDNLAARDFINWLIQTKITDNDWKHNITQ, (SEQ ID NO: 2)

HADGTFISDYSTILDNLAARDFINWLIQTKGTD, (SEQ ID NO: 16)

HADGTFISDYSTILDNLAARDFINWLIQTKIKD, (SEQ ID NO: 17)

HADGTFISDYSTILDNLAARDFINWLIQTKITK, (SEQ ID NO: 18)

HADGTFISDYSKILDNLAARDFINWLIQTKITK, (SEQ ID NO: 27)

HADGTFISDYSTIKDNLAARDFINWLIQTKITK, (SEQ ID NO: 28)

HADGTFISDYSTILDKLAARDFINWLIQTKITK, (SEQ ID NO: 29)

HADGTFISDYSTILDNLKARDFINWLIQTKITK, (SEQ ID NO: 30)

HADGTFISDYSTILDNLAAKDFINWLIQTKITK, (SEQ ID NO: 31)

HADGTFISDYSTILDNLAARDFINWLIQTKGKKNDWKHNITQ, (SEQ ID NO: 32)

HAEGTFISDYSTILDNLAARDFVNWLLAQKITD, (SEQ ID NO: 9)

HAEGTFISDYSTILDNLAARDFINWLIQTKGKK, (SEQ ID NO: 10)

HADGTFISDYSTILDNLAARDFINWLIQTKGKK, (SEQ ID NO: 19)

and a functional variant of any thereof having 1, 2 or 3 individual amino acid substitutions;

d)

(SEQ ID NO: 7)
HAEGTFISDYSIAMDKLAARDFINWLIQTKITD (SEQ ID NO: 8)
HAEGTFISDYSTILDNIHQQDFINWLIQTKITD and a functional variant of any thereof having 1, 2, or 3 individual amino acid substitutions, wherein said functional variant of any of a), b), c) or d) comprises substitution of 0, 1, or 2 of amino acids 5 to 11 of SEQ ID NO:21, wherein said functional variant binds to and activates the GIPR and the GLP-2R, and wherein said peptide:
 a. activates the GIPR with an efficacy ($E_{max}$ values) which is at least 65% of the efficacy by which native GIP activates the GIPR, and
 b. activates the GLP2R with an efficacy ($E_{max}$ values) which is at least 65% of the efficacy by which native GLP-2 activates the GLP2R.

* * * * *

SEQUENCE LISTING

```
<160> NUMBER OF SEQ ID NOS: 33

<210> SEQ ID NO 1
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 1

His Ala Glu Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 2
<211> LENGTH: 42
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(42)

<400> SEQUENCE: 2

His Ala Glu Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp Asn Asp Trp Lys His Asn Ile Thr Gln
        35                  40

<210> SEQ ID NO 3
<211> LENGTH: 33
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: PEPTIDE
<222> LOCATION: (1)..(33)

<400> SEQUENCE: 3

His Ala Asp Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 4
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 4

His Ala Glu Gly Ser Phe Ile Ser Asp Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 5
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 5

His Ala Glu Gly Thr Phe Ser Asp Glu Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 6
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 6

His Ala Glu Gly Thr Phe Ile Ser Asp Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 7
```

```
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 7

His Ala Glu Gly Thr Phe Ile Ser Asp Tyr Ser Ile Ala Met Asp Lys
1               5                   10                  15

Leu Ala Ala Arg Asp Phe Ile Asn Trp Leu Ile Gln Thr Lys Ile Thr
            20                  25                  30

Asp

<210> SEQ ID NO 8
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 8

His Ala Glu Gly Thr Phe Ile Ser Asp Tyr Ser Thr Ile Leu Asp Asn
1               5                   10                  15

Ile His Gln Gln Asp Phe Ile Asn Trp Leu Ile Gln Thr Lys Ile Thr
            20                  25                  30

Asp

<210> SEQ ID NO 9
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 9

His Ala Glu Gly Thr Phe Ile Ser Asp Tyr Ser Thr Ile Leu Asp Asn
1               5                   10                  15

Leu Ala Ala Arg Asp Phe Val Asn Trp Leu Leu Ala Gln Lys Ile Thr
            20                  25                  30

Asp

<210> SEQ ID NO 10
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 10

His Ala Glu Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Gly Lys
            20                  25                  30
```

Lys

```
<210> SEQ ID NO 11
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 11
```

His Gly Asp Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp

```
<210> SEQ ID NO 12
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 12
```

His Val Asp Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp

```
<210> SEQ ID NO 13
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 13
```

His Ala Asp Gly Thr Phe Ser Ser Asp Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp

```
<210> SEQ ID NO 14
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 14
```

His Ala Asp Gly Thr Phe Ile Asp Asp Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 15
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 15

His Ala Asp Gly Thr Phe Ile Ser Glu Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 16
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 16

His Ala Asp Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Gly Thr
            20                  25                  30

Asp

<210> SEQ ID NO 17
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 17

His Ala Asp Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Ile Lys
            20                  25                  30

Asp

<210> SEQ ID NO 18
<211> LENGTH: 33
<212> TYPE: PRT
<213> ORGANISM: Artificial Sequence
<220> FEATURE:
<223> OTHER INFORMATION: Synthetic peptide
<220> FEATURE:

```
<221> NAME/KEY: PEPTIDE
<222> LOCATION: (1)..(33)

<400> SEQUENCE: 18

His Ala Asp Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Lys

<210> SEQ ID NO 19
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 19

His Ala Asp Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Gly Lys
            20                  25                  30

Lys

<210> SEQ ID NO 20
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)
<220> FEATURE:
<221> NAME/KEY: misc_feature
<222> LOCATION: (2)..(2)
<223> OTHER INFORMATION: Xaa is Ala, Gly, or Val
<220> FEATURE:
<221> NAME/KEY: misc_feature
<222> LOCATION: (3)..(3)
<223> OTHER INFORMATION: Xaa is Asp or Glu
<220> FEATURE:
<221> NAME/KEY: misc_feature
<222> LOCATION: (5)..(5)
<223> OTHER INFORMATION: Xaa is Thr or Ser
<220> FEATURE:
<221> NAME/KEY: misc_feature
<222> LOCATION: (7)..(7)
<223> OTHER INFORMATION: Xaa is Ile or Ser
<220> FEATURE:
<221> NAME/KEY: misc_feature
<222> LOCATION: (8)..(8)
<223> OTHER INFORMATION: Xaa is Ser or Asp
<220> FEATURE:
<221> NAME/KEY: misc_feature
<222> LOCATION: (9)..(9)
<223> OTHER INFORMATION: Xaa is Asp or Glu
<220> FEATURE:
<221> NAME/KEY: misc_feature
<222> LOCATION: (10)..(10)
<223> OTHER INFORMATION: Xaa is Tyr or Met
<220> FEATURE:
<221> NAME/KEY: misc_feature
<222> LOCATION: (11)..(11)
<223> OTHER INFORMATION: Xaa is Ser or Asn
<220> FEATURE:
<221> NAME/KEY: misc_feature
<222> LOCATION: (12)..(12)
```

<223> OTHER INFORMATION: Xaa is Tyr or Ile
<220> FEATURE:
<221> NAME/KEY: misc_feature
<222> LOCATION: (13)..(13)
<223> OTHER INFORMATION: Xaa is Ile or Ala
<220> FEATURE:
<221> NAME/KEY: misc_feature
<222> LOCATION: (14)..(14)
<223> OTHER INFORMATION: Xaa is Leu or Met
<220> FEATURE:
<221> NAME/KEY: misc_feature
<222> LOCATION: (16)..(16)
<223> OTHER INFORMATION: Xaa is Asn or Lys
<220> FEATURE:
<221> NAME/KEY: misc_feature
<222> LOCATION: (23)..(23)
<223> OTHER INFORMATION: Xaa is Ile or Val
<220> FEATURE:
<221> NAME/KEY: misc_feature
<222> LOCATION: (27)..(27)
<223> OTHER INFORMATION: Xaa is Ile or Leu
<220> FEATURE:
<221> NAME/KEY: misc_feature
<222> LOCATION: (28)..(28)
<223> OTHER INFORMATION: Xaa is Gln or Ala
<220> FEATURE:
<221> NAME/KEY: misc_feature
<222> LOCATION: (29)..(29)
<223> OTHER INFORMATION: Xaa is Thr or Gln
<220> FEATURE:
<221> NAME/KEY: misc_feature
<222> LOCATION: (31)..(31)
<223> OTHER INFORMATION: Xaa is Ile or Gly
<220> FEATURE:
<221> NAME/KEY: misc_feature
<222> LOCATION: (32)..(32)
<223> OTHER INFORMATION: Xaa is Tyr or Lys
<220> FEATURE:
<221> NAME/KEY: misc_feature
<222> LOCATION: (33)..(33)
<223> OTHER INFORMATION: Xaa is Asp or Lys

<400> SEQUENCE: 20

His Xaa Xaa Gly Xaa Phe Xaa Xaa Xaa Xaa Xaa Xaa Xaa Asp Xaa
1               5                   10                  15
Leu Ala Ala Arg Asp Phe Xaa Asn Trp Leu Xaa Xaa Xaa Lys Xaa Xaa
                20                  25                  30
Xaa

<210> SEQ ID NO 21
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)
<220> FEATURE:
<221> NAME/KEY: MISC_FEATURE
<222> LOCATION: (2)..(2)
<223> OTHER INFORMATION: Xaa is Ala or Gly
<220> FEATURE:
<221> NAME/KEY: MISC_FEATURE
<222> LOCATION: (3)..(3)
<223> OTHER INFORMATION: Xaa is Asp or Glu
<220> FEATURE:
<221> NAME/KEY: MISC_FEATURE
<222> LOCATION: (23)..(23)
<223> OTHER INFORMATION: Xaa is Ile or Val
<220> FEATURE:
<221> NAME/KEY: MISC_FEATURE
<222> LOCATION: (27)..(27)
<223> OTHER INFORMATION: Xaa is Ile or Val
<220> FEATURE:

```
<221> NAME/KEY: MISC_FEATURE
<222> LOCATION: (28)..(28)
<223> OTHER INFORMATION: Xaa is Gln or Ala
<220> FEATURE:
<221> NAME/KEY: MISC_FEATURE
<222> LOCATION: (29)..(29)
<223> OTHER INFORMATION: Xaa is Thr or Gln
<220> FEATURE:
<221> NAME/KEY: MISC_FEATURE
<222> LOCATION: (31)..(31)
<223> OTHER INFORMATION: Xaa is Ile or Gly
<220> FEATURE:
<221> NAME/KEY: MISC_FEATURE
<222> LOCATION: (32)..(32)
<223> OTHER INFORMATION: Xaa is Thr or Lys
<220> FEATURE:
<221> NAME/KEY: MISC_FEATURE
<222> LOCATION: (33)..(33)
<223> OTHER INFORMATION: Xaa is Asp or Lys

<400> SEQUENCE: 21

His Xaa Xaa Gly Thr Phe Ile Ser Asp Tyr Ser Thr Ile Leu Asp Asn
1               5                   10                  15

Leu Ala Ala Arg Asp Phe Xaa Asn Trp Leu Xaa Xaa Xaa Lys Xaa Xaa
            20                  25                  30

Xaa

<210> SEQ ID NO 22
<211> LENGTH: 42
<212> TYPE: PRT
<213> ORGANISM: Homo sapiens

<400> SEQUENCE: 22

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 23
<211> LENGTH: 33
<212> TYPE: PRT
<213> ORGANISM: Homo sapiens

<400> SEQUENCE: 23

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 24
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)
<220> FEATURE:
<221> NAME/KEY: MISC_FEATURE
<222> LOCATION: (2)..(2)
<223> OTHER INFORMATION: Xaa is Ala, Gly, or Val

<400> SEQUENCE: 24
```

```
His Xaa Asp Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp
```

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(9)

<400> SEQUENCE: 25

```
Asn Asp Trp Lys His Asn Ile Thr Gln
1               5
```

<210> SEQ ID NO 26
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 26

```
His Ala Asp Gly Thr Phe Ser Ser Asp Tyr Ser Thr Ile Leu Asp Asn
1               5                   10                  15

Leu Ala Ala Lys Asp Phe Ile Asn Trp Leu Ile Gln Thr Lys Ile Thr
            20                  25                  30

Asp
```

<210> SEQ ID NO 27
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 27

```
His Ala Asp Gly Thr Phe Ile Ser Asp Tyr Ser Lys Ile Leu Asp Asn
1               5                   10                  15

Leu Ala Ala Arg Asp Phe Ile Asn Trp Leu Ile Gln Thr Lys Ile Thr
            20                  25                  30

Lys
```

<210> SEQ ID NO 28
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 28

His Ala Asp Gly Thr Phe Ile Ser Asp Tyr Ser Thr Ile Lys Asp Asn
1               5                   10                  15

Leu Ala Ala Arg Asp Phe Ile Asn Trp Leu Ile Gln Thr Lys Ile Thr
            20                  25                  30

Lys

<210> SEQ ID NO 29
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 29

His Ala Asp Gly Thr Phe Ile Ser Asp Tyr Ser Thr Ile Leu Asp Lys
1               5                   10                  15

Leu Ala Ala Arg Asp Phe Ile Asn Trp Leu Ile Gln Thr Lys Ile Thr
            20                  25                  30

Lys

<210> SEQ ID NO 30
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 30

His Ala Asp Gly Thr Phe Ile Ser Asp Tyr Ser Thr Ile Leu Asp Asn
1               5                   10                  15

Leu Lys Ala Arg Asp Phe Ile Asn Trp Leu Ile Gln Thr Lys Ile Thr
            20                  25                  30

Lys

<210> SEQ ID NO 31
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)

<400> SEQUENCE: 31

His Ala Asp Gly Thr Phe Ile Ser Asp Tyr Ser Thr Ile Leu Asp Asn
1               5                   10                  15

Leu Ala Ala Lys Asp Phe Ile Asn Trp Leu Ile Gln Thr Lys Ile Thr
            20                  25                  30

Lys

<210> SEQ ID NO 32
<211> LENGTH: 42
<212> TYPE: PRT
<213> ORGANISM: Artificial Sequence
<220> FEATURE:
<223> OTHER INFORMATION: Synthetic peptide

```
<220> FEATURE:
<221> NAME/KEY: PEPTIDE
<222> LOCATION: (1)..(42)

<400> SEQUENCE: 32

His Ala Asp Gly Thr Phe Ile Ser Asp Tyr Ser Thr Ile Leu Asp Asn
1               5                   10                  15

Leu Ala Ala Arg Asp Phe Ile Asn Trp Leu Ile Gln Thr Lys Gly Lys
                20                  25                  30

Lys Asn Asp Trp Lys His Asn Ile Thr Gln
            35                  40

<210> SEQ ID NO 33
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(33)
<220> FEATURE:
<221> NAME/KEY: MISC_FEATURE
<222> LOCATION: (2)..(2)
<223> OTHER INFORMATION: Xaa is Ala, Gly, or Val
<220> FEATURE:
<221> NAME/KEY: MISC_FEATURE
<222> LOCATION: (3)..(3)
<223> OTHER INFORMATION: Xaa is Asp or Glu
<220> FEATURE:
<221> NAME/KEY: MISC_FEATURE
<222> LOCATION: (5)..(5)
<223> OTHER INFORMATION: Xaa is Thr or Ser
<220> FEATURE:
<221> NAME/KEY: MISC_FEATURE
<222> LOCATION: (7)..(7)
<223> OTHER INFORMATION: Xaa is Ile or Ser
<220> FEATURE:
<221> NAME/KEY: MISC_FEATURE
<222> LOCATION: (8)..(8)
<223> OTHER INFORMATION: Xaa is Ser or Asp
<220> FEATURE:
<221> NAME/KEY: MISC_FEATURE
<222> LOCATION: (9)..(9)
<223> OTHER INFORMATION: Xaa is Asp or Glu
<220> FEATURE:
<221> NAME/KEY: MISC_FEATURE
<222> LOCATION: (10)..(10)
<223> OTHER INFORMATION: Xaa is Tyr or Met
<220> FEATURE:
<221> NAME/KEY: MISC_FEATURE
<222> LOCATION: (11)..(11)
<223> OTHER INFORMATION: Xaa is Ser or Asn
<220> FEATURE:
<221> NAME/KEY: MISC_FEATURE
<222> LOCATION: (12)..(12)
<223> OTHER INFORMATION: Xaa is Thr or Ile or Lys
<220> FEATURE:
<221> NAME/KEY: MISC_FEATURE
<222> LOCATION: (13)..(13)
<223> OTHER INFORMATION: Xaa is Ile or Ala
<220> FEATURE:
<221> NAME/KEY: MISC_FEATURE
<222> LOCATION: (14)..(14)
<223> OTHER INFORMATION: Xaa is Leu, Met, or Lys
<220> FEATURE:
<221> NAME/KEY: MISC_FEATURE
<222> LOCATION: (16)..(16)
<223> OTHER INFORMATION: Xaa is Asn or Lys
<220> FEATURE:
<221> NAME/KEY: MISC_FEATURE
<222> LOCATION: (18)..(18)
<223> OTHER INFORMATION: Xaa is Ala or Lys
<220> FEATURE:
<221> NAME/KEY: MISC_FEATURE
```

```
<222> LOCATION: (20)..(20)
<223> OTHER INFORMATION: Xaa is Ala or Lys
<220> FEATURE:
<221> NAME/KEY: MISC_FEATURE
<222> LOCATION: (23)..(23)
<223> OTHER INFORMATION: Xaa is Ile or Val
<220> FEATURE:
<221> NAME/KEY: MISC_FEATURE
<222> LOCATION: (27)..(27)
<223> OTHER INFORMATION: Xaa is Ile or Val
<220> FEATURE:
<221> NAME/KEY: MISC_FEATURE
<222> LOCATION: (28)..(28)
<223> OTHER INFORMATION: Xaa is Gln or Ala
<220> FEATURE:
<221> NAME/KEY: MISC_FEATURE
<222> LOCATION: (29)..(29)
<223> OTHER INFORMATION: Xaa is Thr or Gln
<220> FEATURE:
<221> NAME/KEY: MISC_FEATURE
<222> LOCATION: (31)..(31)
<223> OTHER INFORMATION: Xaa is Ile or Gly
<220> FEATURE:
<221> NAME/KEY: MISC_FEATURE
<222> LOCATION: (32)..(32)
<223> OTHER INFORMATION: Xaa is Thr or Lys
<220> FEATURE:
<221> NAME/KEY: MISC_FEATURE
<222> LOCATION: (33)..(33)
<223> OTHER INFORMATION: Xaa is Asp or Lys

<400> SEQUENCE: 33

His Xaa Xaa Gly Xaa Phe Xaa Xaa Xaa Xaa Xaa Xaa Xaa Asp Xaa
1               5                   10                  15

Leu Xaa Ala Xaa Asp Phe Xaa Asn Trp Leu Xaa Xaa Xaa Lys Xaa Xaa
            20                  25                  30

Xaa
```